United States Patent [19]

Preziosi et al.

[11] Patent Number: 4,788,151

[45] Date of Patent: Nov. 29, 1988

[54] METAL COMPLEXED ACETYLENIC COMPOUNDS USEFUL AS ENVIRONMENTAL INDICATING MATERIALS

[75] Inventors: Anthony F. Preziosi, Ledgewood; Thaddeus Prusik, Roosevelt, both of N.J.

[73] Assignee: LifeLines Technology, Inc., Morris Plains, N.J.

[21] Appl. No.: 912,711

[22] Filed: Sep. 29, 1986

[51] Int. Cl.$^4$ .................. G01K 11/16; G01N 31/22; C07C 127/15

[52] U.S. Cl. .................................. 436/2; 116/206; 116/207; 116/217; 252/408.1; 260/96.5 R; 422/56; 422/57; 422/58; 556/81; 556/110; 556/118

[58] Field of Search .................. 436/2; 422/56–58; 252/408.1; 116/206, 207, 217; 556/81, 110, 118; 260/96.5 R

[56] References Cited

U.S. PATENT DOCUMENTS

| 3,501,303 | 3/1970 | Foltz et al. |
| 3,743,505 | 7/1973 | Bloom et al. |
| 3,999,946 | 12/1976 | Patel et al. |
| 4,125,534 | 11/1978 | Yee |
| 4,189,399 | 2/1980 | Patel |
| 4,208,186 | 6/1980 | Patel |
| 4,208,501 | 6/1980 | Yee et al. |
| 4,215,208 | 7/1980 | Yee et al. |
| 4,235,108 | 11/1980 | Patel |
| 4,238,352 | 12/1980 | Patel |
| 4,276,190 | 6/1981 | Patel |
| 4,278,561 | 7/1981 | Yee |
| 4,373,032 | 2/1983 | Preziosi et al. |
| 4,389,217 | 6/1983 | Baughman et al. |
| 4,439,346 | 3/1984 | Patel et al. |

OTHER PUBLICATIONS

G. Wegner, "Topochemical Polymerization of Monomers with Conjugated Triple Bonds"–Die Makromolekulare Chemie 154 (1972) 35–48.

Primary Examiner—Barry S. Richman
Assistant Examiner—Jill Johnston
Attorney, Agent, or Firm—Arthur J. Plantamura

[57] ABSTRACT

Acetylenic complexes are disclosed that are useful as environmental indicating materials whereby exposure thereof to environmental stimuli induces a color change. These complexes contain at least one effective complexing metal and at least one acetylenic compound of the general formula:

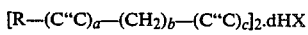

$$[R-(C\text{``}C)_a-(CH_2)_b-(C\text{``}C)_c]_2 \cdot dHX$$

Wherein a is 1 or 2, b is about 0–5; c is 0 or 1; with the proviso that when a is 1, b and c are 0, when a is 2, b is about 0–5 and c is 0 or 1; and R is $-(CH_2)_n-NHC(O)NHR'$; wherein n is an integer of about 1 to 10; and R' is selected from the group consisting of: (a) hydrogen; (b) cycloalkyl; (c) alkenyl; (d) cycloalkenyl; (e) alkyl; (f) phenyl; (g) alkoxy; (h) alkoxy alkyl; and (i) alkoxycarbonylalkyl.

25 Claims, No Drawings

METAL COMPLEXED ACETYLENIC COMPOUNDS USEFUL AS ENVIRONMENTAL INDICATING MATERIALS

DESCRIPTION

1. Field of the Invention

An aspect of this invention relates to a novel class of acetylenic complexes comprising a combination acetylenic compound and complexing metal; said complexes are capable of undergoing one or more color changes when exposed to environmental stimuli, and thus useful as environmental indicating materials. Another aspect of this invention relates to environmental indicating devices comprising such complexes, and to the methods of using such devices and complexes to determine environmental changes.

2. Background of the Invention

As is typical with acetylenic compounds, the acetylenic complexes of the invention change color in response to environmental stimuli due to polymerization of their acetylenic moieties via 1,4 addition reactions upon exposure to such environmental stimuli.

Acetylenic compounds that undergo color changes in response to some stimulii are known to the art. For example, acetylenic compounds having at least one —C≡CC—C≡C—, have been disclosed as time-temperature history indicators in U.S. Pat. No. 3,999,946 (Patel et al.). Patel et al. discloses monomeric acetylenic compounds of the formula, R—C≡C—C≡C—R, where R includes an alkyl, aryl, benzoate, sulfonate, urethane, acid or alcohol moiety. The compounds disclosed by Patel et al. are colorless and are polymerizable in the solid state, either thermally or by actinic radiation. As the polymerization proceeds, these compounds undergo a contrasting color change to blue or red, and in some instances the color intensifies with time until the compounds finally develop into metallic-looking polymers. Thus, the compounds can be used as time-temperature history indicators and as radiation-dosage indicators. The reference also described polymers of the type [—C≡C—CH$_2$)$_m$OCONH(HC$_2$)$_6$N-HOCO(CH$_2$)$_m$—C≡C—]$_n$ where m is 2, 3 or 4 and n is large, wherein a polymer containing polymeric repeating units of the same empirical formula, undergoes color changes upon thermal annealing.

Other exemplary U.S. patents relating to acetylenic compounds and their use as environmental indicating materials include U.S. Pat. Nos. 4,215,208 (thermochromic materials), 4,125,534 (carbazolyl diacetylenes), and 4,189,399 (co-crystallized compositions).

G. Wegner in an article entitled "Topochemical Polymerization of Monomers with Conjugated Triple Bonds" in Die Makromolekulare Chemie 154, pp. 35–48 (1972) discloses acetylenic compounds having at least one —C C—C C— moiety and two urea moieties, the urea moieties being separated from the diacetylene by a phenylene moiety. However, the compounds disclosed by Wegner were not very reactive and did not exhibit color changes that would be useful in monitoring environmental exposure.

None of the publications disclose or suggest complexation of acetylenic compounds to produce acetylenic complexes whose reactivity to environmental stimuli is amenable to control. Acetylenic compounds in the art usually display reactivity immediately after synthesis, thus requiring special handling during processing and shipping of articles fabricated from them. Certain of the complexes of the present invention provide a solution to this problem, as complexation provides an alteration in the reactivity of the acetylenic compounds contained in the complexes, even to the extent of complete inactivity. Reactivity is then reinstated at the desired time point by contact with an appropriate reactivating agent.

In other embodiments of the present invention, the reactivity of acetylenic compounds to stimuli is enhanced upon complexation. In further embodiments of the present invention, complexes react spontaneously with moisture, undergoing a readily perceptible color change, thus making them quite useful in moisture indicators.

BRIEF DESCRIPTION OF THE INVENTION

This invention relates to an acetylenic complex comprising at least one effective complexing metal and at least one acetylenic compound of the general formula:

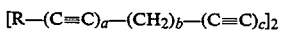

Wherein:
a is 1 or 2, b is about 0–5, c is 0 or 1; with the proviso that when a is 1, b and c are 0, when a is 2, b is about 0–5 and c is 0 or 1; and R is:

Wherein:
(1) n is an integer of about 1 to 10; and
(2) R' is selected from the group consisting of:
  (a) hydrogen;
  (b) cycloalkyl;
  (c) alkenyl;
  (d) cycloalkenyl;
  (e) alkyl;
  (f) phenyl;
  (g) alkoxy;
  (h) alkoxyalkyl; and
  (i) alkoxylcarbonylalkyl;

The present invention also provides a method whereby the activity of acetylenic compounds to environmental stimuli may be altered or controlled by contacting the compound with an effective complexing metal to produce a derivative of the compound. Further provided are environmental indicating devices comprising the acetylenic complexes of the invention, and methods using such devices to assess environmental changes.

DETAILED DESCRIPTION OF THE INVENTION

This invention relates to novel acetylenic complexes that are particularly useful for monitoring the environmental exposure of various products that undergo progressive quality changes upon environmental exposure to environmental stimuli. Environmental stimuli includes such stimuli as temperature, cumulative time-temperature, moisture, pressure, and radiation exposure.

An "effective complexing metal" in the present invention is one that is capable of altering the reactivity of the acetylenic compounds contained in the complexes of the invention in response to stimuli so that the reactivity of the complex to stimuli differs from that of the acetylenic compound in the absence of complexation. This alteration may take may forms, including but not limited to, enhancing the activity of the acetylenic compounds in response to various stimuli, and achieving activity in response to stimuli with compounds previously inactive to such stimuli. Other alterations include reversibly inactivating compounds previously active to stimuli. The complexes may then be reactivated prior to exposure to such stimuli. A further modification is the alteration of acetylenic compounds by complexing, resulting in a complex capable of spontaneously reacting to moisture, as evidenced by a color change.

While the present inventors do not wish to be bound by any theory, it is believed that the effective complexing metals of the present invention are those whose cations complex with the acetylenic compound. This complexation exerts control over the activity of the acetylenic compound by altering the 1,4-addition reaction of the acetylenic moieties, resulting in a new reactivity, or an enhancement, reduction or complete suspension of an existing reactivity.

Suitable agents to accomplish this purpose vary widely and may be selected from various types of metals. Preferred among the metals are those from Group IA, Group II A and the transition elements of the Periodic Chart. It is particularly preferred that these metals be derived from salts, limited only in that the metal salt and the acetylenic diureas have appreciable solubility in a common solvent. Illustrative of the metals particularly useful as complexing agents are potassium, sodium, rubidium, lithium, cesium, magnesium, calcium, strontium, iron, cobalt, nickel, copper, zinc, cadmium, and tin.

Of the salts that the metals may be derived from may be mentioned salts of the chloride, bromide, and iodide. Of these, salts of the chloride are preferred.

The preferred agents for complexation are metals from Groups I and II of the Periodic table derived from salts, particularly magnesium, calcium, and strontium, and lithium, and most particularly chloride salts of these.

The metal salt must be at least partially soluble in a solvent for the diurea compound, complete solubility being generally preferred. Especially preferred is solubility in polar solvents such as the organic acids and alcohols. Illustrative of these are acetic acid, propionic acid, butanoic acid, pentanoic acid, hexanoic acid, heptanoic acid, octanoic acid, and the disubstituted acids corresponding to these; alcohols such as methanol, ethanol, propanol, butanol, pentanol, ethoxyethanol, isopropanol, and the like. Also useful as common solvents are the highly polar solvents such as dimethylsulfoxide, dimethylformamide, and the like. Preferred among the solvents in general are acetic acid and propionic acid due to the high solubility of most of the metal salts and the diurea compound in these solvents.

The properties of the acetylenic complexes of the present invention are discussed in more detail hereinbelow following the description of preferred urea acetylenic compounds and methods for their syntheses.

Acetytenic compounds for use in the practice of the invention are those of the general formula:

[R—(C≡C)$_a$—(CH$_2$)$_b$—(C≡C)—$_c$]$_2$

Wherein:
a is 1 or 2, b is about 0-5, c is 0 or 1; with the proviso that when a is 1, b and c are 0, when a is 2, b is about 0-5 and c is 0 or 1; and R is —(CH$_2$)$_n$—NHC(O)NHR'

Wherein:
(1) n is an integer of about 1 to 10; and
(2) R' is selected from the group consisting of:
  (a) hydrogen;
  (b) cycloalkyl;
  (c) alkenyl;
  (d) cycloalkenyl;
  (e) alkyl;
  (f) phenyl;
  (g) alkoxy;
  (h) alkoxy alkyl; and
  (i) alkoxy carbonylalkyl;

The preferred acetylenic compounds in the complexes of this invention are of the general structures I, II, and III as depicted hereinbelow. Structure I represents the most preferred family of compounds and is as follows:

$$[\text{R'}-\text{NH}-\overset{\overset{\text{O}}{\|}}{\text{C}}-\text{NH}-(\text{CH}_2)_n-\text{C}\equiv\text{C}-]_2$$

wherein n is an integer of 1-10; R' is an organic moiety comprising one or more moieties selected from the group comprising a cycloalkyl moiety of about 3-7 carbon atoms, an alkenyl moiety of about 3-18 carbon atoms, a cycloalkenyl moiety of about 3-7 carbon atoms, an alkoxy moiety of about 2-18 carbon atoms, a linear or branched alkyl moiety of about 1 to 18 carbon atoms, an alkoxycarbonylmethylene moiety of about 3-14 carbon atoms, or a phenyl moiety.

In many preferred embodiments of the invention, R' is a linear or branched alkyl moiety of about 1-18 carbon atoms, an alkoxycarbonylmethylene moiety of about 1-12 carbon atoms or a phenyl moiety. The linear or branched alkyl moieties are especially preferred. Especially preferred alkyl moieties include ethyl, n-propyl, n-butyl, n-hexyl, n-octyl, n-decyl, n-dodecyl and n-octadecyl. Especially preferred alkoxycarbonylmethylene moieties include ethoxycarbonylmethylene and butoxycarbonylmethylene. With respect to all compounds of structure I, n is preferably 1-4 and more preferably 1.

Other preferred acetylenic compounds of this invention include the split (diacetylenic moieties separated by alkyl groups) tetraynes and hexaynes. The split tetraynes and hexaynes are illustrated by general Structures II and III as follows:

$$[\text{R'}-\text{NH}-\overset{\overset{\text{O}}{\|}}{\text{C}}-\text{NH}-(\text{CH}_2)_{\overline{n}}\text{C}\equiv\text{C}-\text{C}\equiv\text{C}_{\overline{b}}(\text{CH}_2)_b]_{\overline{2}}^- \quad \text{II}$$

$$[\text{R'}-\text{NH}-\overset{\overset{\text{O}}{\|}}{\text{C}}-\text{NH}-(\text{CH}_2)_{\overline{n}}\text{C}\equiv\text{C}-\text{C}\equiv\text{C}-(\text{CH}_2)_{\overline{b}}\text{C}\equiv\text{C}]_{\overline{2}}^- \quad \text{III}$$

wherein R' is as described for Structure I; wherein n is an integer from about 1 to 4, and b is an integer of about 1 to 6.

Syntheses of the acetylenic compounds in the novel complexes of this invention may be easily accomplished by employing procedures which are well known by those having skill in the art of organic chemistry. For example, in the acetylenic complexes compounds of general structure I wherein n=1, the most preferred group of compounds in the complex may be synthesized by the following two step reaction scheme:

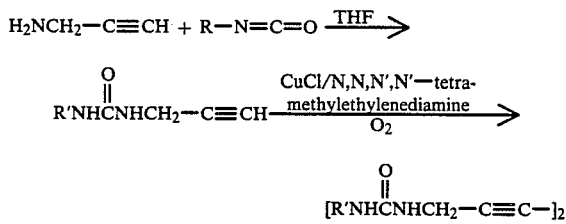

wherein R' is as described hereinabove. In the above synthetic route, monopropargylamine is reacted with a suitable isocyanate (i.e., having the desired R' group conforming to the R' groups as described for compounds of general structure I) in the presence of tetrahydrofuran or other similar solvent such as 2-methoxyethyl ether to form an alkyne intermediate having a urea moiety and the desired R' group. The first reaction shown above will occur at temperatures between about 25° C. and about 50° C. and requires a reaction time between about 1 and about 2 hours. A catalyst is not required for the reaction. Thereafter, without isolation of the intermediate, the intermediate is oxidatively coupled via conventional procedures to produce the final product. The oxidative coupling reaction may be conducted at temperatures between about 25° C. and about 50° C. and will generally require only about 2 to about 4 hours to complete. Isolation of the product from the reaction mixture may be accomplished by conventional precipitation, filtration, and recrystallization procedures etc. However, recrystallization for some compounds from certain solvents results in indicator materials of varying reactivity, even before complexing.

Syntheses of compounds in the complex of Structure I wherein $n=2-10$ is somewhat more complex, but conventional procedures are also available for production of compounds of this nature. These compounds may be formed by a five step reaction scheme that initially involves oxidatively coupling an acetylenic compound having a terminal hydroxyl moiety such as 3-butyn-1-ol, 4-pentyn-1-ol, 5-hexyn-1-ol or the like to the corresponding diyn-diol. The diyn-diol is then reacted with p-toluene sulfonyl chloride to form a bis(p-toluenesulfonate) compound. This reaction employs tetrahydrofuran or another similar solvent as a reaction medium and pyridine is employed as a promoter. The diyn-bis(p-toluenesulfonate) compounds are then converted to diphthalimido-diyn compounds using a Gabriel type synthesis as described in an article entitled "The Gabriel Synthesis of Primary Amines," *Angew. Chem. Internat. Edit.*, 7,919 (1968) by M. S. Gibson and R. W. Bradshaw, said article being incorporated herein by reference. Thereafter, the dipthalimido-diyn compounds are hydrolyzed via a two stage hydrolysis to produce a diyn-diamine salt. The two-stage hydrolysis that should preferably be employed is also described in the Gibson and Bradshaw article. Finally, the diyn-diamine may be reacted with a suitable isocyanate, $R-N=C=O$, in accordance with the procedures described herein where $n=4$ to produce the diurea having the desired R groups and $n=2-10$.

Syntheses of the tetraynes in the complexes of general structure II and the hexaynes in the complexes of general structure III is preferably accomplished by the following reaction scheme:

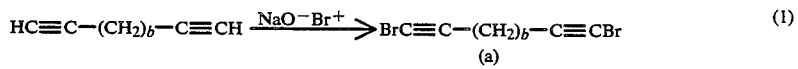  (1)

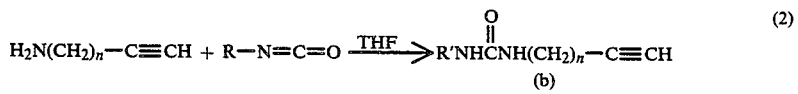  (2)

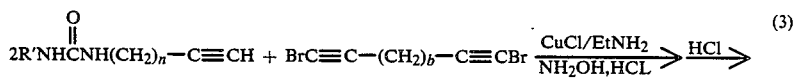  (3)

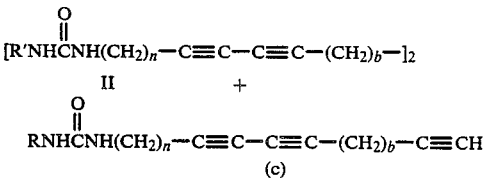

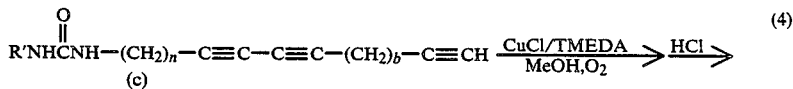  (4)

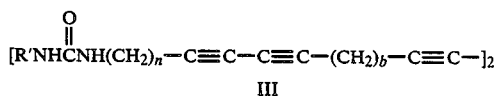

In reaction (1) above a diyne having $b=1-6$ is reacted with a suitable hypobromite such as sodium hypobromite to produce a dibromo diyne compound (a). Reaction (2) involves reacting an alkyne having a terminal primary amine wherein $n=1-10$ with an isocyanate having a suitable R' group as described hereinabove to produce urea (b) having a terminal acetylene moiety and desired R' group. Thereafter, compounds (a) and (b) are coupled by reaction in the presence of a solution comprising CuCl, n-ethylamine and hydroxylamine hydrochloride to produce tetraynes, of general structure II. This coupling reaction is more particularly illustrated in Example 12. The triyne (c) in the above reaction scheme may be extracted from the reaction medium by addition of a nonpolar solvent such as petroleum ether, heptane, or hexane or the like. Thereafter, triyne (c) may be oxidatively coupled to hexaynes of general structure III by well known procedures in accordance with reaction 4 above.

The polymerization reactivity of many of the acetylenic diureas in the complexes of the present invention may be increased or decreased by dissolving two or more of the compounds in a heated common solvent such as an organic acid, illustrative of which are acetic acid, propionic acid, butanoic acid, and the like; alcohols, ethoxyethanols, 2,6-lutidine, chlorobenzene, pyridine, and the like. The solvated compounds are then recrystallized to produce a cocrystallized composition. To avoid polymer particle formation, it is preferred to first subject each of the compounds it is desired to co-crystallize to a recrystallization procedure and then add the compounds in this recrystallized form to the heated common solvent for the co-crystallization procedure.

In carrying out the co-crystallization procecure, it is preferable that the solvent be heated to about 15° C. to about 20° C. below its boiling point. Adding the compositions to the solvent in this heated state, and then cooling at a moderate rate, avoids premature 1,4 polymerization of the diurea compound. The relative amounts of compounds in a co-crystallized composition may vary widely, however, it is preferred that a stoichiometric ratio be established between the components prior to co-crystallization.

The co-crystallized compositions may be described as a solid solution, i.e., an intimate mixture on the molecular level. Co-crystallization may be further distinguished from simple physical mixtures of the individual compounds, in that the co-crystallized composition exhibits a substantially different polymerization reactivity and subsequent rate of color change upon exposure to actinic radiation or thermal annealing. The simple mixture will exhibit properties which are merely an additive combination of the individual compounds, depending upon the properties of each compound present.

A preferred co-crystallized composition for purposes of the present invention is that of the ethyl and propyl urea derivatives, due to the enhancement of color reactivity when this co-crystallized composition is exposed to environmental stimuli as compared to the reactivity of each of the components individually. To achieve the most preferred enhancement of color reactivity, a mole ratio of about 1:2 based on the amount of propyl derivative to ethyl is particularly useful, especially when acetic acid is employed as the common solvent.

The complexes of the present invention are obtained by treatment of the acetylenic compounds with the various complexing metals. This treatment may be effected by techniques conventional to the art. The preferred methods of obtaining the complexes of the present invention include dissolution and recrystallization techniques.

The diurea compound and a compound containing complexing metal ion may be added to the solvent together or separately for dissolution. However, it is preferred in most cases that the metal in a salt form be added to the solvent first, to insure complete solvation of the metal moiety. The solvent should preferably be in a heated state upon addition of the metal complexing agent, especially at about 15° C. to 20° C. below its boiling point.

After the addition of metal salt, the solvent may be maintained at its elevated temperature or recooled before the addition of the diurea. For purposes of preventing premature 1,4-polymerization of the diurea, however, it is preferred to maintain the solvent containing the metal salt at about 15° C. to 20° C. below its boiling point.

Once both of the components are dissolved, the temperature of the system is cooled to about room temperature by any convenient means, in some cases by simply leaving the solution at ambient temperature for a period of time or contacting it with a water bath, ice bath, and the like. Upon cooling, a particulate product is usually formed which may then be filtered or washed to remove excess solvent. Solvents useful for this optional washing are preferably those that will avoid decomplexation, exemplary of which are ethanol and the higher alcohols, as well as non-hydrolytic solvents, and the like.

Superior color responsiveness to environmental stimuli, in particular cumulative time/temperature stimuli, may be prefereably achieved with the complexes of the present invention wherein R' of the general acetylenic compound Structures I, II, and III is a linear alkyl moiety or alkoxycarbonylmethylene moiety of about 1 to 12 carbon atoms; preferably about 1-9 carbon atoms. To achieve this superior color responsiveness, it is particularly preferred to complex with salts of metals from Groups IA and IIA, most especially $MgCl_2$, $LiCl_2$ and $CaCl_2$. When these particular salts are used, mole ratios of salt to monomer in the reaction media should generally range from about 0.5:1 to about 4:1, preferably about 2:1 to about 4:1.

Color responsiveness to environmental stimuli unattainable prior to complexation may be achieved upon complexation of certain of the compounds. This occurs when R' in the general acetylenic compound Structures I, II, and III is an organic moiety of about 1-5 carbon atoms, preferably about 1-3 carbon atoms, and most preferably the methyl or isopropanol moiety. In a particularly preferred embodiment, the acetylenic compound is the isopropyl derivative, and the complexing agent is $CaCl_2$.

Certain complexes of the present invention demonstrate sensitivity to moisture. Particularly preferred moisture sensitive complexes may be obtained from complexation of acetylenic compounds of general Structures I, II, and III wherein R' is a linear moiety of about 1-9 carbon atoms, particularly about 4-8 carbon atoms. In particularly preferred embodiments, the acetylenic derivatives are complexed with a large excess of $CaCl_2$. The complexes are then activated by thermal or actinic radiation, such as ultraviolet, gamma and the like to affect polymerization via 1,4 addition. However, this activation and resulting polymerization does not evidence the typical blue color indicative of long chain polymers; but rather a red color. Then the color may change to orange when contacted with water making them potentially useful in moisture indicators. Thereafter, they may change to blue due to the thermal activity resulting from decomplexation. Color responsiveness to water is a property the acetylenic compounds did not demonstrate prior to complexation.

The moisture sensitive complexes of the present invention offer superior sensitivity in the detection of moisture, as liquid or vapor phases of varying kinds and degrees serves to effect a color change. Ambient moisture may be detected as well as immersion in water or mixtures of water and other components in a liquid phase. Ambient humidity values of above about 30% may readily be detected over a period of hours, with higher humidity values detectable in a matter of minutes. Several factors bear on the moisture sensitivity of the complexes, such as the amount and thickness of the surface area of the complexed compound exposed to the moisture, length of time of the exposure, amount of complexing agent present in a layer of compound exposed to moisture, and the like. One of skill in the art should have no difficulty in optimizing these and other such parameters for desired use.

The moisture sensitivity of the complexed compounds may also be controlled by coating a substrate containing the complexed compound in whole or in part with a layer of polymeric material, such as polyvinyl (chloride), poly(ethylene), polybutadiene, cellulose, or polystyrene, and the like. Such a coating serves to alter the rate at which the moisture reaches the complexed compound. The thickness of such a protective layer governs in part the degree of control exerted over the reactivity to moisture. Generally speaking, the thicker the layer, the more moisture required for reactivity or the longer the time required for absorption of the moisture to evidence the reactivity.

It is within the contemplation of the present invention to utilize the moisture sensitivity properties of the complexes described above in a moisture indicator system. In accordance with one aspect of the present invention, moisture indicators fabricated with the present complexes would preferably be activated from a UV source and protected from moisture until desired use with a protective moisture strip, impermeable packing or any suitable protective measure. When it is desired to use the indicator, the protective measure is simply removed and the indicator exposed.

A superior active-inactive-activatable system is achieved with the complexes of the present invention. Preferred complexes for this purpose comprise the general acetylenic compounds of Structure I, II, and III, where R' is a linear alkyl organic moiety of about 1–5 carbon atoms, preferably about 2 to 3 carbon atoms, and a metal salt complexing agent. Particularly preferred are the acetylenic compounds of Structure I with about 1–3 carbon atoms, especially the ethyl and propyl derivatives, most especially the cocrystallized ethyl and propyl derivatives with a mole ratio of 2:1 respectively. The preferred complexing agent of the invention used in obtaining the active-inactive system is calcium, particularly calcium chloride.

In preparing the inactive-activatable complexes, the standard dissolution and recrystallization techniques may be employed. The diurea compound and the metal salt are dissolved in a common solvent at an elevated temperature, preferably about 15° C. to 20° C. below the boiling point of the solvent. The amount of complexing agent required may vary widely depending on the desired reactivity properties, limited only by the processability characteristics of the complex and compound in solution. To avoid a mixture of uncomplexed material and complexed material, or overcomplexed material that will not recrystallize from solution, it is preferred to use about stoichiometric amounts of the complexing agent to the diurea compound. However, when calculating the appropriate mole ratios, one must take into account the availability of the metal salt in solution, which is governed by the volume. In general, it is preferred to use above about 14 wt % metal salt per 100 mls of solvent, with about 14 wt % to about 18.5 wt % particularly preferred. Then mole ratios of the diurea to the amount of metal salt in solution based on the volume may be calculated. For example, based on 14.4% wt./vol. metal salt solution, mole ratios of complexing agent to the diurea of about 0.4 to 1.0; preferably 0.6 to 1.0 have generally been found to be useful. Mole ratios higher than about 0.6 to 1.0 decrease the amount of recrystallized urea, as it tends to remain in solution. Mole ratios lower than about 0.4 to 1.0 result in a mixture of complexed and uncomplexed acetylenic compound, which may tend to reduce the reactivity of a given amount of compound but not completely deactivate it. However, if this is desirable for some purposes, the mole ratio may be adjusted accordingly.

Reactivation of the above acetylenic compounds whose activity has been diminished completely or in part may be effected by exposing the complex to some stimuli. For example, such reactivation may completely or in part be effected by a hydrolytic process which better coordinates the complexing agent, so that the 1,4 addition reaction may take place. Conventional dissolution and recrystallization techniques may be utilized to accomplish this, by using a variety of solvents that regenerate the original non-complexed alkylene. For example, this may be accomplished by a variety of means such as dissolution and recrystallization from solvents of small molecular size whose affinity for the metal salt is greater than that of the diurea. Hydrolytic solvents are useful for this purpose, illustrative of which are water, alcohols, organic acids and amines. Preferred among these are water or those solvents having lower alkyl chains, particularly methanol, the lower amides, the lower amines, and HCl. Also preferred are N,N,N',N'-Tetramethylethylene diamine, glycerol, and acetic acid combined with water. When acetic acid combined with water is used, it is preferable that the mixture contain at least about 20% water, more preferably about 20%–70% water, and most preferably about 50% water and 50% acetic acid.

Contacting the complex with a solvent vapor may also reactivate the inactivated acetylenic complex, and may be accomplished by conventional methods such as heating or bubbling an inert gas into the solvent source. Useful solvents in this regard may be selected from water, steam, the lower alcohols, organic acids in combination with water, and amines. Particularly preferred are water in combination with acetic acid, with the water content being about 20%–70%.

In their active state, the acetylenic complexes of this invention undergo incremental or progressive color changes upon exposure to environmental stimuli. Thus, there is a corresponding change in reflectance or reflectivity due to exposure to environmental stimuli. Reflectance or reflectivity is defined as the amount of light at selected wavelengths that is reflected by an indicating material after said light has impinged upon the indicating material. A perfectly reflective material has a reflectance or reflectivity equal to one. Percent reflectance or reflectivity is equal to one hundred times the reflectivity. Since the acetylenic ureas undergo reflectivity changes upon exposure to environmental stimuli, said compounds will undergo contrasting color changes upon exposure to given amounts of actinic radiation or thermal annealing. The term "thermal annealing" refers to heating at sufficient temperatures, as by infrared radiation, flame, heat gun, laser-beam, and the like which is sufficiently high to cause polymerization by 1,4-addition of the acetylenic moieties.

In their reactive state, many of the acetylenic urea compounds present in the complexes of this invention undergo a color change from white, pink, or light gray to various shades of blue upon exposure to environmental stimuli and will thus absorb light in a spectral region ranging from about 250 nm to about 700 nm. Thus, environmental indicator labels prepared from the complexes of this invention may be read by optical scanners consisting of a light source capable of illuminating a surface; a detector to sense the amount of reflected light; and a means to output the signal from the optical detector that operate in this spectral region.

Complexes containing alkyl ureas of general Structure I (the most preferred class of compounds) wherein R is a linear or branched alkyl of about 1–18 carbon atoms are especially useful in this respect as most ureas of this nature gradually polymerize to a blue color upon being exposed to environmental stimuli, with speed of polymerization and degree of color response being directly related to the amount of environmental exposure. The complexes are also especially useful because they characteristically either melt at high temperatures, generally above about 170° C., or they do not melt at all but simply rapidly polymerize, resulting in a deep blue color, at temperatures above about 175° C. This is a highly desirable feature in addition to the optimal spectroscopic properties of these compounds, as many of the acetylenic compositions described in the prior art melt at modest temperatures. This is problematic, as melting of a partially polymerized acetylenic composition usually causes a color change which could yield false information regarding cumulative temperature exposures.

The acetylenic complexes of this invention may be fabricated into environmental indicator devices in accordance with well known procedures. An environment indicating device is a device that may be attached in some form to a product that undergoes progressive quality changes in response to environmental exposure, said device being capable of recording the amount of environmental exposure of said product. The acetylenic compounds of this invention record the amount of environmental exposure by color changes that may be determined by visual observation or by optical scanning methods.

Substrates that may be employed for construction of devices that employ the acetylenic ureas or acetylenic complexes of this invention include paper, paperboard, fiberboard, cardboard, Kimdura, Mylar ™, polyethylene, polypropylene, polyacrylate polymers and copolymers, cellulose ethers, cellulose esters, mixed esters or other similar materials. Other exemplary of materials that may be employed as substrates for environmental indicator labels that employ acetylenic ureas include synthetic resins and plastics as described in U.S. Pat. No. 3,501,302. Additionally, it should be appreciated that containers for various products may also serve as substrate upon which the environmental indicator labels are constructed.

The complexes of the invention may be applied to the substrate in various fashions. Preferably, this is accomplished by direct application of the complex to the substrate. For example, an ink solution comprising the acetylenic urea complex and solvent may be sprayed onto the substrate in order to deposit the acetylenic urea complex onto the desired area of the substrate. The solution should include the acetylenic urea complex in an amount comprising about 9% to about 18% and preferably about 14% by weight. Of course, this ink system could be printed by more conventional methods such as flexography, screen, gravure, letter-press, ink-jet printing, or the like.

Solvents that may be employed for forming the above-described ink solutions are those that will not decomplex the acetylenic complex and include acetic acid, propanoic acid, heptanoic acid, nonanoic acid, ethanol, and the higher alcohols, Cellusolve ®, and the like.

Another, and more preferred, method for applying the acetylenic complexes to the indicator device substrates involves initially grinding the acetylenic or complex into fine particles and forming a suspension of the particles in a suitable binder-solvent system. Suitable binders for forming these suspensions include natural and synthetic plastics, resins, waxes, colloids, nonacqueous gels, and the like. The suspension comprising the binder and the acetylenic complex may then be applied to the desired area of the label by spraying, screen printing, gravure, flexography letterpress, or other conventional printing means. This method of applying the acetylenic complex to the substrate employs the acetylenic material as a pigment in a conventional ink. This method is more particularly described by U.S. Pat. No. 3,501,297.

Devices containing the acetylenic complexes of the present invention may be useful in environmental indicating systems. Particularly useful are time-temperature indicators prepared from these compositions, as an inactive-activatable indicator system may be achieved. Indicators fabricated from certain of the complexes of the present invention may be completely inactived, making processing and shipping possible without the need for temperature control. The indicators may then be reactivated by a variety of means as discussed herein. Co-crystallized compositions with enhanced reactivity, suitable for applications in the chilled and frozen areas, are also made inactive-activatable by complexing. Color-responsivity of these devices for environmental indicating systems is now better controlled with the use of complexing.

ACETYLENIC COMPOUND PREPARATION EXAMPLES A–R

General Procedure for Preparing Acetylenic Compounds for Use in the Present Invention A three neck flask fitted with a stirrer, thermometer, $N_2$ flow tube which was exchanged with an $O_2$ dip tube for oxidative coupling reactions, and a dropping funnel was employed for producing the compounds of Examples 1–15. An excess of an isocyanate compound dissolved in tetrahydrofuran (hereinafter referred to as THF) was added dropwise to the reaction flask to which a solution comprising mono-propargylamine and THF had been previously added. Since the reactions were rapid, a catalyst was not employed. To moderate the temperature of the reaction, a water bath (typically 18° C.) was used during the addition of the isocyanate. After 1 to 2 hours, the reaction media was charged with CuCl and complexation agent, N,N,N',N'-tetramethylethylenediamine (hereinafter referred to as TMEDA), followed by a continuous moderate bubbling of $O^2$ to effect the oxidative coupling reaction. A water bath was used to moderate the intitial temperature excursion.

Typically, after 2½ hours, the medium was deactivated with HCl. Purification was effected by filtration, washings, and recrystallization.

In cases where ultraviolet radiation was employed to cause polymerization and corresponding color changes of the acetylenic ureas, the ultraviolet source employed was a model UVS-11E ultraviolet lamp (Ultra Violet Products Inc., Pasadena, Calif.)

EXAMPLE A 2,4-hexadiyn-1,6-bis(ethylurea)

A 1 liter flask was charged with 50 g (0.9 mol) monopropargylamine and 300 mL THF. 89 g(1.25 mol) ethylisocyanate diluted with 50 mL THF was added dropwise over a 30 minute time period. During the addition, the reaction flask was placed in a water bath (18° C.) to moderate the exotherm during the ethylisocyanate addition. The temperature did not exceed 40° C. 2.5 g CuCl and 6 mL TMEDA were added to the reaction media after 1½ hours. Oxygen was bubbled into the reaction medium at a moderate rate while stirring. Initially, a water bath was used to keep the temperature between 25° to 35° C. The waterbath was removed after 15 minutes and the temperature slowly rose to 55° C. and then decreased. After 2½ hours, the medium was deactivated by adding 200 ml/10% HCl solution. The product was filtered, washed with additional HCl solution, followed by washing with $H_2O$. The product was stirred in a solution of 200 mL methanol and 200 mL 10% HCl solution, filtered, washed with $H_2O$, methanol, and finally acetone. The product was recrystallized by dissolving it in 500 mL hot acetic acid at 100° C. while stirring and heating, filtering at 15° C., and cooling to 15°–20° C. in a cold water bath at a moderate rate. The precipitate was filtered, washed with petroleum ether (50°–110° C.) and then vacuum dried for about 1–2 hours. Yield: 88 g (78% of theoretical) fine powder product which turned blue at a moderate rate under ambient conditions, about 25° C., in the dark. The product did not melt when heated to 300° C. on a Mettler hot stage. Upon heating, rapid polymerization to dark blue and then black occurred.

| ELEMENTAL ANALYSIS $C_{12}H_{18}N_4O_2$ (MW = 250.277) | | | | |
|---|---|---|---|---|
| Calcd. | C | 57.59 | H | 7.25 |
|  | N | 22.38 | O | 12.78 |
| Found. | C | 57.47 | H | 7.34 |
|  | N | 22.45 | O | 12.73 |

EXAMPLE B 2,4-hexadiyn-1,6-bis(butylurea)

Same as Example A except 25.8 g (0.25 mol) butylisocyanate diluted with 25 mL THF and 10.0 g (0.18 mol) mono-propargylamine in 100 mL THF was used to synthesize the mono-urea derivative. The complexing agent was derived from 1 g CuCl and 3 mL TMEDA to form the diurea. The reaction media was deactivated with 125 mL HCl (10%). The methanol, acetone, and water used in the work-up were reduced proportionally to Example 1. Yield: 26.6 g (97%) of a greenish product which moderately changed to blue at ambient conditions (about 25° C.) in the dark indicating an active phase.

A 1 g sample was recrystallized from 100 mL ethanol. Initially, the color of the recrystallized product was light pink, but the color slowly changed to orange at ambient conditions (about 25° C.). Upon irradiation for 5–10 seconds with the UV source, the color of the product changed to blue. When recrystallized from acetic acid an orange phase was obtained that intensified upon irradiation with the UV source. However, when the product was recrystallized from ethoxyethanol (1 gm/18 m) followed by recrystallization from acetic acid (1 gm/10 ml), only the blue phase occurred. The orange phase could be converted to the blue phase by heating to approximately 65° C.

| ELEMENTAL ANALYSIS $C_{16}H_{26}N_4O_2$ (MW = 306.385) | | | | |
|---|---|---|---|---|
| Calcd. | C | 62.72 | H | 8.55 |
|  | N | 18.28 | O | 10.44 |
| Found. | C | 62.53 | H | 8.81 |
|  | N | 18.08 | O | 10.01 |

EXAMPLE C 2,4-hexadiyn-1,6-bis(octylurea)

Same as Example A and B except 21.5 g (0.14 mol) octylisocyanante, 6.6 g (0.12 mol) mono-propargylamine, and 200 mL THF were used to synthesize the mono-urea. A proportionally larger amount of THF was necessary to keep the mono-urea solubilized. Synthesis of the monourea required 1 hour at 25° C. 1 g CuCl, 3 mL TMEDA, and 50 mL THF were added to the reaction media for the coupling reaction to obtain the di-urea. The temperature was maintained between 45°–50° C. throughout the reaction. The coupling reaction was complete in 2 hours. Yield: 25.2 g (99%) of light blue product which melted and decomposed at about 195° C. upon heating. The product was recrystallized from ethanol (1 g/40 mL) or acetic acid (1 gm/15 ml). The recrystallized product was thermochromic and underwent a light blue to red-purple reversible transition at 80° C.

| ELEMENTAL ANALYSIS $C_{24}H_{24}N_4O_2$ (MW = 418.626) | | | | |
|---|---|---|---|---|
| Calcd. | C | 68.86 | H | 10.11 |
|  | N | 13.38 | O | 7.64 |
| Found. | C | 68.83 | H | 10.34 |
|  | N | 13.23 | O | 7.60 |

EXAMPLE D 2,4-hexadiyn-1,6-bis(dodecylurea)

Same as Example A and B except 25 g (0.45 mole) monopropargylamine, 100 g (0.47 mole) dodecylisocyanate, 350 mL THF were used to form the mono-urea. After the addition of the isocyanate, the temperature was increased to 45°–50° C. to keep the product solubilized. The reaction was continued for 1 hour at which time 2.5 g CuCl and 6 mL TMEDA were added to the reaction media. The temperature was maintained between 45°–50° C. for 2½ hours; the product precipitated as it formed (the temperature during this reaction should not exceed 50° C. because above 50° C. appreciable polymer formation occurs). The product was deactivated with a 1:1 mixture of 20% HCl solution/MeOH (500 mL), filtered and washed twice with methanol and acetone. The resulting product was yellow. The yellow color intensified upon exposure to ultraviolet light.

Upon placing a sample of the product on filter paper and applying mechanical pressure with a spatula to the product, subsequent UV irradiation or thermal annealing changed the yellow color to blue. It was also found that rapidly heating the yellow phase above about 150° C. results in an abrupt color change from yellow to blue-purple. In order to recrystallize the product, it was added to 2.5 L dimethylsulfoxide, heated to 80°–85° C. on a hot plate, and rapidly brought up to 95° C. before it was removed and filtered. The product was precipitated with 1.3 L ethanol, filtered, and washed with additional ethanol followed by petroleum ether (50°–110° C.). Yield: 112 g (93%) pale to light blue product which melted and decomposed at 215° C. upon heating.

| ELEMENTAL ANALYSIS $C_{32}H_{58}N_4O_2$ (MW = 530.842) | | | |
|---|---|---|---|
| Calcd. C | 72.40 | H | 11.01 |
| N | 10.55 | O | 6.03 |
| Found. C | 72.25 | H | 11.13 |
| N | 10.65 | O | 6.10 |

EXAMPLE E 2,4-hexadiyn-1,6-bis(octadecylurea)

Same as Examples A and B except 10.6 g (0.036 mol) n-octadecylisocyanate, 2.0 g (0.036 mol) mono-propargylamine, and 75 mL THF were used to snythesize the monourea. The reaction proceeded for 1 hour at a temperature between 50° C.–60° C. The coupling reaction was conducted using 0.25 g CuCl and 3 mL TMEDA, allowing the reaction to continue for 2½ hours at 45°–50° C. Yield: 11.8 g (94%) light yellow product which changed to a dark yellow upon exposure to 5–10 seconds of ultravioletradiation. A sample (about 0.5 g) was placed on filter paper. Mechanical pressure (i.e., shearing with spatula) was applied to the product. Following the application of pressure, the product was irradiated with ultraviolet radiation and the color of the product changed from yellow to blue.

EXAMPLE F 2-4-hexadiyn-1,6-bis(n-propylurea)

Same as Examples A and B except 44 g (0.8 mol) mono-propargylamine, 72 g (0.84 mol) n-propylisocyanate, 250 mL THF were employed to synthesize the monourea. The synthesis of the mono-urea required 1 hour. 2.5 g CuCl and 6 mL TMEDA were added for the coupling reaction which was complete in 2½ hours at about 35°–40° C. A yellowish white product which changed to a bright yellow upon exposure to UV radiation was isolated. Recrystallization from 1 l acetic acid resulted in an active phase which changed from pink to blue upon exposure to UV radiation. Yield: 76 g (68%). Upon heating to 300° C., the product decomposed. A melting point was not observed.

| ELEMENTAL ANALYSIS $C_{14}H_{22}N_4O_2$ (MW = 278.356) | | | |
|---|---|---|---|
| Calcd. C | 60.41 | H | 7.97 |
| N | 20.13 | O | 11.50 |
| Found. C | 60.81 | H | 8.11 |
| N | 19.78 | O | 12.22 |

EXAMPLE G 2,4-hexadiyn-1,6-bis(iso-propylurea)

Same as Examples A and B except 25 g (0.45 mol) mono-propargylamine, 150 mL THF were used to synthesize the mono-urea and 2 g CuCl and 6 mL TMEDA were added for the coupling reaction. Yield: 35.5 g (54%) of a white product after recrystallization from 700 ml acetic acid which was inactive both thermally and when treated with UV light which changed to a bright yellow upon exposure to ultraviolet radiation. Recrystallization from various solvents such as ethanol (1 g/170 mL) did not result in an active blue phase when treated with UV light. The product melted and decomposed at 270° C.

| ELEMENTAL ANALYSIS $C_{14}H_{22}N_4O_2$ (MW = 278.356) | | | |
|---|---|---|---|
| Calcd. C | 60.41 | H | 7.97 |
| N | 20.13 | O | 11.50 |
| Found. C | 60.84 | H | 8.09 |
| N | 19.75 | O | 11.93 |

EXAMPLE H 2,4-hexadiyn-1,6-bis(methylurea)

Same as Examples A and B except 2.0 g (0.036 mol) mono-propargylamine, 2.1 g (0.036 mol) methylisocyanate, and 50 mL THF were used to synthesize the mono-urea and 0.25 g CuCl and 2 mL TMEDA were added for the coupling reaction. Synthesis of the monourea required 1 hour at 25° C. The coupling reaction required 2½ hours at 40° C. Yield: 1.7 g (41%) light pinkish white product which changed to bright yellow upon exposure to 5–10 seconds of ultraviolet radiation. Recrystallization from dimethylsulfoxide, ethanol (1 g/250 mL), or acetic acid did not result in an active blue phase. Upon heating, the product melted and decomposed at 255° C.

| ELEMENTAL ANALYSIS $C_{10}H_{14}N_4O_2$ (MW = 222.248) | | | |
|---|---|---|---|
| Calcd. C | 54.02 | H | 6.35 |
| N | 25.21 | O | 14.40 |
| Found. C | 53.96 | H | 6.60 |
| N | 24.48 | O | 13.32 |

EXAMPLE I 2,4-hexadiyn-1,6-bis(ethoxycarbonylmethylene urea)

Same as Examples A and B except 2.0 g (0.036 mol) mono-propargylamine, 4.6 g (0.036 mol) ethylisocyanatoacetate, and 50 mL THF were used for the synthesis of the mono-urea and 0.25 g CuCl and 2 mL TMEDA were added for the coupling reaction. Synthesis of the mono-urea required 1 hour at 25° C. The coupling reaction required 2½ hours at 45° C. Yield: 5.0 g (76%) of a pinkish product which changed to blue upon exposure to 5–10 seconds ultraviolet radiation. Upon heating, the product melted between 190° and 195° C.

| ELEMENTAL ANALYSIS $C_{16}H_{22}N_4O_6$ (MW = 366.374) | | | |
|---|---|---|---|
| Calcd. C | 52.45 | H | 6.05 |

-continued

| ELEMENTAL ANALYSIS $C_{16}H_{22}N_4O_6$ (MW = 366.374) | | | |
|---|---|---|---|
| | N 15.29 | O | 26.20 |
| Found. | C 52.13 | H | 6.05 |
| | N 13.01 | O | 21.61 |

EXAMPLE J 2,4-hexadiyn-1,6-bis(butoxycarbonylmethylene urea)

Same as Examples A and B except 2.0 g (0.036 mol) mono-propargylamine, 5.6 g (0.036 mol) butylisocyanatoacetate, and 50 mL THF were used for the synthesis of the mono-urea and 0.25 g CuCl and 2 mL TMEDA were used for the coupling reaction. Synthesis of the mono-urea required 1 hour at 25° C. The coupling reaction required 1½ hours at 45° C. Yield: 3.9 g (51%) of a white product was obtained by recrystallization of the product from ethanol (1 g/75 mL).

A sample of the product turned blue upon exposure to 5–10 seconds of ultraviolet radiation. Upon heating, a sample of the product melted at 168°–169° C. and turned red upon cooling and solidification. The cooled and solidified product turned blue upon exposure to 5–10 seconds of ultraviolet radiation.

| ELEMENTAL ANALYSIS $C_{16}H_{22}N_4O_6$ (MW = 422.482) | | | |
|---|---|---|---|
| Calcd. | C 56.86 | H | 7.16 |
| | N 13.26 | O | 22.72 |
| Found. | C 57.07 | H | 7.67 |
| | N 13.01 | O | 21.61 |

EXAMPLE K 2,4-hexadiyn-1,6-bis(phenylurea)

Same as Examples A and B except 5.5 g (0.1 mole, 6.2 mL) monopropargylamine, 14.9 g (0.125 mole) phenylisocyanate, and 100 mL THF were used to synthesize the mono-urea and 0.25 g CuCl and 2.5 g TMEDA were used for the coupling reaction. Synthesis of the mono-urea required 1½ hours at 25° C. The coupling reaction was complete in 2½ hours at 35° C. Yield: 10.5 g (61%) of a white product. Upon exposure to ultraviolet radiation for 1–2 minutes the product underwent a color change from white to light blue. Upon heating to 275° C. the product melted and decomposed.

EXAMPLE L

Synthesis of 2,4,8,10-dodecyltetrayn-1,12,-bis(ethylurea)

This compound was produced by a 3 step synthesis that involved preparing two reactants, 1,6-dibromo-1,5-hexadiyne and 1-propyn-3-ethylurea, and then oxidatively coupling the two reactants.

1,6-dibromo-1,5-hexadiyne was prepared in the following manner

Sodium hypobromite, NaOBr, was prepared by incrementally adding 120 g (0.732 mole, 39.0 mL) bromine to a 6.35N NaOH solution composed of 76.2 g (1.95 mole) NaOH in 300 mL aqueous cooled to 0° C. The solution was stirred for approximately ½ hours. The solution was added dropwise over a 30 minute period to 1,5-hexadiyne 23.4 g (0.30 mole) and 100 mL H₂O contained in a 1 liter 3-necked flask which was fitted with a mechanical stirrer, thermometer, N₂ flow tube to blanket the reactants, and an ice-bath. The temperature was kept below 18° C. throughout the additions. After 3 hours, the solid product was extracted with 100 mL diethylether, washed with H₂O and then kept over 25 g ammonium chloride until needed.

1-propyn-3-ethylurea was prepared in the following manner: To a 500 mL flask fitted with a stirrer, thermometer, N₂ flow tube, and a dropping funnel, 75 mL THF and 5.5 g (0.1 mole, 6.9 mL) monopropargylamine was added followed by the dropwise addition of 7.1 g (0.1 mole) ethylisocyanate in 10 mL THF; the temperature was initially moderated with a water bath and continued for 1 hour at room temperature.

In order to oxidatively couple 1,6-dibromo-1,5-hexadiyne and 1-propyn-3-ethylurea to thereby produce 2,4,8,10-dodecyltetrayn-1,12-bis(ethylurea), 0.2 g CuCl, 15 mL n-ethylamine (70%) followed by 1.5 g NH₂OH.HCl was added to the reaction media containing the urea. 13.5 g (0.058 mole) 1,6-dibromo-1,5-hexadiyne in 25 mL THF was then added dropwise to the reaction media over a 20 minute period. Initially, the reaction media was cooled with a cold water bath so that the temperature did not exceed 40° C. during the addition. Thereafter, the bath was removed and the reaction was continued with stirring for 2 hours at a temperature of 25° C. Product precipitation occurred during the addition of the dibromohexadiyne. The product was filtered and washed with several small portions of THF (50 mL total), followed by removal and saving of the substrate. The product was washed twice with a 10% HCl solution, followed by H₂O washings and finally washing with methanol and dried. Yield: 12.1 g (74.2%) pale blue product which changed to dark blue upon exposure to 5–10 seconds ultraviolet radiation. Upon continued irradiation (i.e, 4 minutes), the product changed to a metallic gold color at a moderate rate. The product did not melt when heated to 300° C. When heated beyond 300° C., it changed to red, then black, then decomposed.

EXAMPLE M

Synthesis of 1,5,7-nonatriyn-9-ethylurea

This compound, a triyne, was recovered from the saved filtrate of the oxidative coupling reaction of Example L. Addition of petroleum ether (50°–110° C.) to the filtrate caused precipitation of a brown product which was washed with 10% HCl followed by H₂O. The product was recrystallized from acetone/petroleum ether (50°–110° C.). Yield: 3.5 g (34.5%) of a white product which changed to red upon exposure to 5–10 seconds of ultra violet radiation.

| ELEMENTAL ANALYSIS $C_{12}H_{14}N_2O$ (202.257) | | | | |
|---|---|---|---|---|
| Calcd C 71.26 | H 6.98 | N 13.85 | O 7.91 | |
| Found C 69.70 | H 7.08 | N 13.84 | O 7.67 | Br 1.7 |

Elemental analysis indicates that 6% of the total theoretically possible bromide remained unhydrolysed.

EXAMPLE N

Synthesis of 2,4,8,10,14,16-Octadecylhexayn-1,18-bis(ethylurea)

This compound was obtained by oxidatively coupling the triyne of Example M. Using the method described in Example A, 1.0 g (0.005 mol) 1,5,7-ethylurea was coupled in a complex composed of 0.25 g CuCl, 2.5 mL TMEDA, and 75 mL methanol, with oxygen being bubbled into reaction media at a moderate rate. The temperature of the reaction media was raised to 60° C. during the initial 5-10 minutes of the reaction time and then heating was discontinued. After 1 hour, 75 mL water was then added. Thereafter, the reaction media was filtered to recover the product. The product was washed with water, HCl (10%) and then water. The product was recrystallized from 125 mL acetic acid. Yield: 0.5 g (50%) of a light pink product which changed to a blue color upon being irradiated with UV light for 5-10 seconds After 30 seconds of irradiation, the product changed to a blueblack color.

| ELEMENTAL ANALYSIS $C_{24}H_{26}N_4O_2$ (MW 402.5) | | | | |
|---|---|---|---|---|
| Calcd. | C | 71.62 | H | 6.51 |
| | N | 13.92 | O | 7.95 |
| Found. | C | 71.13 | H | 6.75 |

EXAMPLE O

Synthesis of 5,7-dodecadiyn-1,12-bis(ethylurea)

This compound was synthesized via the following 5 step reaction sequence:

(a) oxidatively coupling 5-hexyn-1-ol to produce 5,7-dodecadiyn-1,12 diol;

(b) reacting the product of (a) with p-toluenesulfonylchloride to produce 5-7-dodecadiyn- 1,12-bis(p-toluenexulfonate);

(c) reacting the product of (b) with potassium phthalimide to produce 1,12-diphthalimido-5,7-dodecadiyne;

(d) subjecting the product of (c) to a two stage hydrolysis (i.e., base hydrolysis followed by acid hydrolysis) followed by treatment with a base to produce 5-7-dodecadiyn-1,12-diamine;

(e) reacting the product of (d) with ethylisocyanate to produce 5,7-dodecadiyn-1,12-bis(ethylurea).

Reaction steps a–e were conducted as follows:

(a) A 1 liter 3-necked flask was charged with 150 mL methanol, 15 mL TMEDA, and 9 g CuCl. 150 mL 5-hexyn-1-ol was oxidatively coupled using the Hay method by adding it dropwise to the reaction media over a 45 minute time period while oxygen was being bubbled into the reaction media. During the addition, the temperature of the media rose to approximately 60° C., then subsided. Oxygen was bubbled into the reaction media for an additional 15 hours before isolation of the product. Isolation: 800 mL chilled water was added to precipitate the product. The product was filtered and washed with additional water. Recrystallization: The product was dissolved in 100 mL methanol and 5 to 10 mL TMEDA. Precipitation was effected by adding chilled water (8°-11° C.). After filtration and washing with water, the product was recrystallized, again. After removal of most of the water, the product was washed with heptane three times and dried under vacuum. Yield: 120 g of a fluffy white product (b) 150 mL pyridine was added dropwise to a solution composed of 58.2 g (0.3 mole) 5,7-dodecadiyn-1,12-diol, (produced from reaction step (a)), 150 g (0.78 mole) p-toluenesulfonylchloride, and 150 mL THF over a 0.5 hour period at a temperature of 20° to 25° C. The reaction was continued with stirring for 6.5 hours at a temperature of 25°-30° C. Isolation: The product was obtained by pouring the reaction media into 1 liter chilled water followed by filtration and several water washings. Recrystallization: The particulate was dissolved in 1.5 liters methanol and refrigerated at −8° C. Thereafter, it was filtered, washed with petroleum ether (50°-110° C.), and vacuum dried. Yield: 110 g (73%) of a light tan product which changed to red upon exposure to 5-10 seconds of ultraviolet radiation. The product had a melting range of 58.5°-59.8° C.

(c) 32.0 g (0.064 mole) 5,7-dodecadiyn-1,12-bis(p-toluenesulfonate) from reaction step (b) and 32.0 g (0.17 mole) potassium phthalimide were reacted in dimethylsulfoxide at 123°-128° C. for 0.5 hours. The reaction media was cooled to 75° C. and 250 mL water was added to precipitate the product. The product was filtered, washed several times with boiling water, acetone, and then heptane. Yield: 24.6 g (85%) of a light tan fine powdered product (d) 10 g (0.022 mole) 1,12-diphthalimido-5,7-dodecadiyne, from reaction step (c), 50 mL $H_2O$, 3.1 g (0.055 mole) KOH, 5 mL pyridine and 80 mL ethanol were refluxed for 1 hour then cooled to 50° C.

(e) 30 mL 10N HCl (0.3 mole) was added incrementally to the reaction media followed by 1 g ZnCl, and refluxed for 3 hours. During the refluxing a product began precipitating (probably the phthalic acid). Isolation: Thereafter, the solvent was reduced by 75%. 100 mL $H_2O$ was added to the reaction media, boiled, filtered, and washed with 50 mL additional boiling $H_2O$. (The filtrant contained 2.5 g (33% of theoretical) phthalic acid; the filtrate contained the diamine-acid salt, $(ClH_3NCH_2-C\equiv C-)_2$, and was observed as two phase separated layers both of which contain the diamine-acid. If the solvent is evaporated from the dark brown layer, a solid forms which changes to blue slowly. The addition of water transforms the blue solid to red). 50 mL 5N NaOH (10 g, 0.25 mole) was added incrementally to the filtrate to neutralize the diamineacid and generate the diamine. After cooling to 30° C., the diamine was extracted with diethylether (150 mL) by shaking. The ether was distilled leaving 2.5 g yellow semi-viscous crude product.

(f) To the crude product of step (e), 50 mL THF and 3 g of $MgSO_4$ (anhydrous) were added. The solution was filtered and 3.2 g (0.045 mole) ethylisocyanate was added in one-shot at room temperature (25° C.). A solid was added to fully precipitate the product. It was filtered and washed with heptane. Yield: 1.8 g (25% of theoretical) white product which changes to blue slowly in daylight. When exposed to UV light, it changes to dark blue within 15 seconds time. The product was confirmed by IR and elemental analyses. Additional product was obtained by adding 200 mL xylene to the dark viscous layer of the filtrate after pouring off the top layer, boiling, then filtering through MgSO. After cooling to 50° C., 3.2 g (0.045 mole) ethylisocyanate was added. The product (containing both symmetrical and unsymmetrical compounds) was precipitated with heptane after ½ hour, filtered, and washed with additional heptane. Yield: 2.1 g crude white product which changes to blue slowly in daylight and dark blue within 30 seconds under a UV lamp.

EXAMPLE P

COLOR RESPONSE BROADENING FROM CO-CRYSTALLIZATION

A solution composed of 1.2 g 2,4-hexadiyn-1,6-bis(ethylurea) (hereinafter referred to as 1KE) in 60 mL acetic acid was prepared; likewise a solution composed of 1.2 g 2,4-hexadiyn-1,6-bis(butylurea) (hereinafter referred to as 1KB) was also prepared. The solutions were mixed in the proportions shown in Table I and precipitated with an equal volume (about 10 mL) of petroleum ether (50°-110° C.), filtered and dried. The color responses of the co-crystalized composition were visually monitored. After 3 days at ambient conditions (about 25° C.) in the dark the co-crystallized compositions were assigned a relative reactivity value from 1 to 4.

TABLE I

Visual Color Response and Relative Reactivity for Co-Crystallized 1KE and 1KB

| Soln 1KE (mls) | Soln 1KB (mls) | 1KE (%) | 1KB (%) | Visual Color Response After 3 days | Relative Reactivity |
|---|---|---|---|---|---|
| 10.0 | 0.0 | 100 | 0 | light gray blue | 3 |
| 9.5 | 0.5 | 95 | 5 | light to med. blue | 1 (most reactive) |
| 9.0 | 1.0 | 90 | 10 | blue light to light med. blue | 2 |
| 5.0 | 5.0 | 50 | 50 | off-white | |
| 1.0 | 9.0 | 10 | 90 | off-white | |
| 0.5 | 9.5 | 5 | 95 | pale blue | |
| 0.0 | 10.0 | 0 | 100 | yellow-orange | 4 |

EXAMPLE Q

Characterization of Incremental Reflectivity Changes

An ink was formed by mixing 12.5 grams of 2,4-hexadiyn-1,6-bis(ethylurea) (1KE) with 36 ml of n-butanol and grinding this mixture in a ball mill for 16 hours. 10 grams of this suspension was mixed with 22.5 grams of a 12% (w/w) solution of Ethocell 45 dissolved in n-butanol. A portion of the ink was diluted so that the diluted ink had an acetylenic concentration that was only one half of the acetylenic concentration of the non-diluted ink.

A number of indicator labels were prepared by printing a rectangular image (0.3 cm×2.1 cm) on pressure sensitive white labels with the ink. A solid black bar(0.2 cm×2.1 cm) was printed on each side of the acetylenic urea bar at distance of 0.2 cm from the outer edge of the acetylenic urea bar. Thus, a white space 0.2 cm wide was between the acetylenic urea bar and the black bars. Thereafter, the labels were placed in controlled temperature baths (i.e. 60° C., 40° C., and 30° C.), and removed periodically in order to determine the reflectance of the indicator after exposure to a given temperature for a given period of time. Upon removal of the indicators from the temperature controlled compartments, each indicator was scanned with an Intermec 1401 scanning wand. The signal generated was forwarded through an amplifier (Signal Control Module T 22050, Skan-a-matic Corp.) and into a TECH LAB I computer. The signal was processed by averaging the reflectance values of the white (W) sections and black (B) bars and the reflectance values of the acetylenic urea bars (AC) as $$R = \frac{AC - B}{W - B}.$$

This value was used to determine the reflectance of the acetylenic urea compound relative to the white and black reference colors. These data are presented in Tables I, II, and III.

TABLE I

Temperature 60° C.

| Time (Days) | Indicator 1 % Reflectance | Indicator 2* % Reflectance |
|---|---|---|
| 0 | 99 | 98 |
| 0.11 | 94 | — |
| 0.25 | 90 | — |
| 0.37 | 83 | 92 |
| 0.59 | 77 | 87 |
| 1.08 | 64 | 78 |
| 1.97 | 39 | 59 |
| 2.91 | 25 | 44 |
| 3.68 | 17 | 33 |
| 4.41 | 12 | 27 |
| 4.71 | | 25 |

*Indicator 2 had an acetylenic urea concentration equal to one half that of Indicator 1.

TABLE II

Temperature 40° C.

| Time (Days) | Indicator 3* % Reflectance | Time (Days) | Indicator 4* % Reflectance |
|---|---|---|---|
| 0 | 98 | .0 | 98 |
| 0.11 | 99 | 0.11 | — |
| 1.01 | 95 | 1.01 | — |
| 1.81 | 94 | 1.81 | 96 |
| 2.03 | 93 | 4.84 | 93 |
| 2.52 | 93 | 5.33 | 90 |
| 9.35 | 76 | 12.16 | 81 |
| 20.43 | 53 | 18.37 | 71 |
| 24.64 | 46 | 23.24 | 61 |
| a | 15 | 27.45 | 57 |
| | | b | 26 |

*Indicator 4 had an acetylenic urea concentration equal to that of Indicator 2, Indicator 3 had an acetylenic urea concentration equal to that of Indicator 1.
a - stored for 49 additional hours at 60° C.
b - stored for 49 additional hours at 60° C.

TABLE III

Temperature 30° C.

| Time (Days) | Indicator 5* % Reflectance | Indicator 6* % Reflectance |
|---|---|---|
| 0 | 99 | 98 |
| 3.8 | 95 | 98 |
| 24.0 | 86 | 93 |
| 63.9 | 66 | 80 |

*Indicator 6 had a acetylenic urea concentration equal to that of Indicator 2, Indicator 5 had an acetylenic urea concentration equal to that of Indicator 1.

The data in Tables, I, II, and III illustrate that percent reflectance is a function of time, temperature and concentration of indicating material, with higher temperatures, longer exposures and higher concentrations of indicating materials resulting in a more rapid decrease in reflectance. Using the data in Tables I and II, an activation energy of 29 kcal/mol was determined for 1-KE. The activation energy was calculated from these data by determining the time necessary to reach a given reflectance value at two temperatures using a form of the Arrhenius equation.

EXAMPLE R

Color Characterization

1KE and 2,4-hexadiyn-1,6-bis(butylurea) (1KB) inks having a concentration equal to the non-diluted 1-KE ink of Example Q were produced as in Example Q. 1 cm diameter dots of these inks were screen printed on Kimdura substrate. Thereafter, the dot indicators were placed on a Mettler hot stage for varying lengths of time at 110° C. and 90° C. The colors of the dot indicators exposed to these temperatures for varying lengths of time were correlated with the Munsell Color Code. The results appear in Tables IV and V.

TABLE IV

| | Temperature 110° C. | |
|---|---|---|
| Time (min.) | Munsell Color Code | Munsell Color Code |
| 0 | 10PB 8/2 | 2.5P 9/2 |
| 6 | 10PB 6/4 | 10PB 4/8 |
| 11 | 10PB 4/6 | 7.5PB 4/8 |
| 24 | 2.5P 3/4 | 5PB 3/8 |
| 31 | 2.5P 2.5/4 | 5PB 3/8 |
| 42 | 2.5P 2.5/2 | 5PB 3/6 |
| 53 | 5P 2.5/2 | 5PB 3/6 |
| 64 | 10PB 3/1 | 5PB 3/6 |
| 100 | 5R 2.5/1 | 5PB 3/6 |
| 118 | 54R 2.5/1 | 5PB 3/4 |
| 139 | — | 5PB 3/4 |
| 203 | — | 5PB 3/4 |
| 251 | | 5PB 3/2 |

TABLE V

| | Temperature 90° C. | |
|---|---|---|
| Time (min.) | 1KE Munsell Color Code | 1KB Munsell Color Code |
| 0 | 5PB 8/1 | 2.5P 9/2 |
| 6 | 5P 7/4 | 2.5PB 5/6 |
| 18 | 2.5P 6/6 | 7.5PB 4/6 |
| 38 | 5P 5/6 | 7.5PB 4/6 |
| 104 | 2.5P 3/8 | 7/5PB 3/6 |
| 133 | 2.5PB 3/8 | 7.5PB 3/4 |
| 170 | 2.5PB 3/4 | 7.5PB 3/4 |
| 192 | 2.5 2.5/4 | 7.5PB 3/4 |
| 230 | 7.5PB 2.5/4 | 7.5PB 3/4 |

The results of Examples Q and R illustrate that 1KE and 1KB can be employed to monitor a wide variety of perishable products, or processes. For example, the data of Example Q demonstrate that 1KE can be employed to monitor a product with a shelf-life of about 1.5–3 years at 25° C., The results also demonstrate that by increasing the acetylenic urea concentration one can monitor periods of time of one year or shorter at room temperature. The results of Example R demonstrate that the color changes associated with the compounds tested could be used to verify that foodstuff cans have been properly sterilized by thermal treatment, as some cans for this purpose are subjected to temperatures in the 90° C.–100° C. range for 10–30 minutes for sterilization purposes.

EXAMPLE S

Co-crystallization of 1KE with 1KPR (the ethyl and propyl derivatives, respectively of Structure I) and reflectance characterization.

Procedure

1KPR and 1KE was added to 10 ml acetic acid at 100° C. in various ratios totalling 1 g for the combined 1KPR and 1KE components. When the temperature reached the boiling point (110°–115° C.) of the media, they were cooled to 20° C. in a cold water bath while stirring. The precipitate was filtered, washed with petroleum ether (50°–110° C.), and air dried. Samples of the products were simultaneously thermally annealed on a Mettler Hot Stage at 90° C. and compared for their color-response along with 1KPR and 1KE controls. Table II indicates the results.

TABLE II

THERMAL COLOR RESPONSE FOR CO-CRYSTALLIZED 1KPR/1KE USING VARIOUS RATIO OF THE TWO COMPONENTS IN ACETIC ACID AT 90° C.

| CODE | RATIO 1KPR:1KE | COLOR RESPONSE AFTER 15 MIN | 30 MIN | RELATIVE REACTIVITY |
|---|---|---|---|---|
| KX320(111) | 1:1 | med. to dark blue | dark blue | 5 |
| KX320(211) | 2:1 | lt. blue | lt. to med. blue | 3 |
| KX321(121) | 1:2 | dark blue | black-blue | 6 most reactive |
| KX320(191) | 1:9 | med. blue | dark blue | 6, less than above |
| KX320(911) | 9:1 | lt. blue | lt. to med. blue | 2 |
| Control | — | med. blue | med. to dark blue | 4, control |
| Control | — | lt. blue | lt. to med. blue | 1, least reactive |

Results

The KX32(121) hereafter referred to as the standard KX32(121), gave the fastest color-response, followed by KX32(191). The least reactive was the 1KPR. The importance of the above findings is not only that the KX32(121) and KX32(191) are highly reactive but rather both of these compounds respond by a gradual color change at 4° C., whereas the others do not, and can be used for chill applications.

The standard KX32(121) was formulated into an ink and coated on a series of bar-coded substrates. Testing at 4° C. gave the following % reflectance values using an integrated scanner.

3 days, 85%
12 days, 53%
7 days, 73%
21 days, 39%
11 days, 60%
35 days, 21%

The reflectance values are dependent on the coating weight and therefore will vary accordingly.

X-ray analysis indicated the formation of a solid-solution rather than mixtures of the two components. NMR proton analysis verified the ratios used, especially the standard KX32(121).

ACETYLENIC COMPLEX EXAMPLES

EXAMPLE I

GENERAL CONCENTRATION EFFECTS OF $CaCl_2$ SOLUTE FOR OBTAINING INACTIVATED 1KE; NOVEL INACTIVE-ACTIVATABLE METALLIC SALT INDICATOR

Conditions necessary to form metallic alts of 1KE and the resultant effects on color-response were investigated. Ideally, a system which could be inactivated and then reactivated without loss of color-response properties was desired. Three experiments testing 1KE and CaCl₂ in Cellosolve ® (ethoxyethanol) and methanol (MeOH) were tried and are summarized as follows.

A small amount of CaCl₂ was added separately to approximately 10 mls Cellosolve and MeOH. After dissolution, a small amount (0.5 g) 1KE was added and heated to a boil. Initially, during the heat-up the 1KE dissolved then precipitated as the temperature was raised. By contrast, dissolution in MeOH occurred without precipitation. A sample from each solution was then set on a filter paper substrate and dried with heat. Upon exposure to UV light the samples changed to blue.

The above was repeated with a large excess of CaCl₂ in MeOH. This resulted in a coated substrate that was insensitive to UV light, evidenced by a change to a light yellow-tan rather than blue. Adding water to a freshly coated substrate followed by UV exposure resulted in the development of a blue color.

EXAMPLE II

INVESTIGATION OF PREFERRED PARAMETERS TO OBTAIN THE INACTIVE FORM OF 1KE/CaCl₂/MeOH PROCEDURE

MeOH (10 ml) was added to each of 5×50 Erlenmeyer flasks. CaCl₂ was added separately to each of the 5 flasks in the mole ratios of 0.25:1, 1:1, 2:1, 4:1, and 8:1 between the CaCl₂ and 1KE, and the combination dissolved in the MeOH media by heating. For the 0.25:1 and 1:1 ratios, the 1KE did not dissolve completely, whereas for the other ratios it did. Test: a few drops of solution from each flask were set in a filter paper simultaneously, dried then set under a UV lamp for 60 seconds. The results are reported in Table III.

TABLE III

MOLE RATIO (CaCl₂:1KE) AND CONCENTRATION (CaCl₂/MeOH) PARAMETERS FOR OBTAINING AN INACTIVE SYSTEM FOR THE 1KE/CaCl₂MeOH INDICATOR

| Sample | CaCl₂ (g, mol) | Mole Ratio CaCl₂:1KE | conc. (wt %) CaCl₂ in MeOH | Soluble (Hot) | Inactive |
|---|---|---|---|---|---|
| 1 | 0.05 g (0.0005 mol) | 0.25:1 | 0.5 | No | No |
| 2 | 0.22 g (0.002 mol) | 1:1 | 2.2 | No | No |
| 3 | 0.44 g (0.004 mol) | 2:1 | 4.4 | Yes | No |
| 4 | 0.89 g (0.008 mol) | 4:1 | 9 | Yes | No |
| 5 | 1.8 g (0.016 mol) | 8:1 | 18 | Yes | Yes |

Note:
(0.5 g, 0.002 mol) 1KE was used.

Results (1) The 0.25:1 and the 1:1 (mole ratio between CaCl₂:1KE) medias (sample #1 and #2) did not solubilize completely. The 2:1 ratio between the CaCl₂ and 1KE, respectively, had a few undissolved particles, and thus might represent a lower limit of solubility for the 1KE. The 4:1 and 8:1 ratios solubilized very easily.

(2) The only sample that did not change to blue under a UV source was the 8:1 media (sample #5). After treating it with water and resetting under the UV lamp a blue color was observed.

Conclusion

An inactive-activatable indicator is obtained when the concentration of the CaCl₂ in MeOH is above about 9%, and the mole ratio between the CaCl₂:1KE is above about 4:1.

EXPERIMENT IV

EFFECTS OF SOLVENT VARIATION ON THE ISOLATION AND COLOR RESPONSIVE ACTIVITY FOR THE 1KE/CaCl₂ INDICATOR SYSTEM

Procedure

4×50 ml Erlenmeyer flasks were charged with 1.8 g (0.016 mol) CaCl₂ then singly with 10 ml of one of the following solvents: acetone, isopropyl alcohol, distilled H₂O, and acetic acid. The flasks were heated so as to solubilize the CaCl₂; all dissolved except the flask containing the acetone which was discarded 0.5 g (0.002 mol) 1KE was added to each flask and heated for dissolution.

Results

1. The 1KE did not dissolve in the heated H₂O media.
2. In the acetic acid media, the 1KE dissolved when heated and remained solubilized when cooled to 25° C.
3. A large portion (possibly all meaning that some precipitation results after complexation with the CaCl₂) of the 1KE dissolved in the isopropyl alcohol when heated to a boil. On cooling, it precipitated into a thick particulated media. It was filtered, washed with small portions of isopropyl alcohol then vacuum dried at 25° C.

Testing (1) A few drops of the acetic acid media was set on a substrate and dried with a heat gun. A blue color was not noted under a UV lamp until it was activated by adding H₂O.

(2) The isolated isopropanol sample also remained inactive under a UV lamp until treated with water.

EXPERIMENT V

CO-CRYSTALLIZATION OF 1KPR/1KE/CaCl₂ VARYING THE CONCENTRATION (WT %) IN ACETIC ACID AND THE WT/WT RATIO BETWEEN 1KPR/1KE IN ISOPROPANOL (IPA) AND COMPARING THEM TO STANDARD KX32(121)

Co-crystallization of 1KPR with 1KE in a 1:1 ratio and 1:2 ratio, in an isopropanol media was tested.

Since it is reasonable to assume that the metal ions, $Ca^{2+}$, disrupt the normal H-bonding and are replaced by stronger ion-dipole bonding, the 1KPR/1KE concentration was increased, minimizing the relative concentration of the metallic ions which could cause interference during H-bonding reorganization after reactivation. Since 1KPR and 1KE are less soluble in isopranol as compared to acetic acid, isopropanol was used for the experiments in Procedure 1 and acetic acid was used for the experiments in Procedure 2.

PROCEDURE 1

4 solutions containing 15 ml isopropanol (IPA) and 1.8 g (0.016 mol, 12 wt %) $CaCl_2$ were prepared. Heating was employed to dissolve most of the salt. A total of 0.5 g di-urea solute was used for each solution. Two control samples contained 0.5 g 1KE and 0.5 g 1KPR, respectively. The remaining two samples contained 1:1 and 1:2 wt/wt ratio of 1KPR and 1KE, respectively. The diureas were heated in the $CaCl_2$/IPA solutions. The 1KE sample dissolved and precipitated almost simultaneously during the heat-up. The 1KPR did not seem to dissolve completely though this could be deceiving, in that simultaneous dissolution and precipitation may have occurred. The other two samples, containing the 1:2 and 1:1 mixtures of 1KPR and 1KE, appeared similar to the 1KE and 1KPR samples and were cooled to 25° C., filtered, washed with small amounts of IPA, and vacuum dried (25° C.); all appeared white in color.

Testing (1) A sample from each of the above products were set under a UV lamp; none changed to blue indicating that they were in the inactive salt form.
(2) A small sample from each was set on a filter paper and activated by adding water (distilled) then thermally annealed along with untreated standard (STD) 1KE and 1KPR. The comparative results are given in Table IV.

TABLE IV

COMPARATIVE COLOR-RESPONSE BETWEEN THE 1:1 AND 1:2 wt/wt RATIO OF THE INACTIVE 1KPR/1KE/CaCl₂/IPA INDICATOR DERIVATIVE AFTER REACTIVATION WITH STANDARD 1KE AND 1KPR AND ALSO INACTIVE 1KE/CaCl₂/IPA AND 1KPR/CaCl₂/IPA AFTER ACTIVATION AT 80° C. ON A METTLER HOT STAGE Comparative

| Sample | Yields (g) | Activity |
|---|---|---|
| 1KE (STD) | — | 3 |
| 1KPR (STD) | — | 1 (lowest) |
| 1KE/CaCl₂/IPA | 1.5 | 2 |
| 1KPR/CaCl₂/IPA | 1.7 | 1.5 |
| 1KPR:1KE(1:1)/CaCl₂/IPA | 1.5 | 3 |
| 1KPR:1KE(1:2)/CaCl₂/IPA* | 1.3 | 3.5 (highest) |

Results

Although the 1KPR:1KE(1:2)/CaCl₂/IPA indicated the highest activity, it was much slower than KX32 (121); the highest activity co-crystallized indicator.

*Contains same 1KPR:1KE weight ratio as noncomplexed KX32(121).

Procedure 2

(1) Initially, the extent of solubility of 1KE was obtained by heating a solution composed of 10 ml acetic acid and 1.8 g (0.016 mol, 18 wt %) $CaCl_2$ and incrementally adding 1 g increments of 1KE to the hot stirred solution. This was continued until 8 g 1KE had been added for a $CaCl_2$:1KE mole ratio of 0.5:1. Surprisingly, no product precipitated after cooling to 25° C. but remained as a thick gel. The solvent could not be removed even under vacuum (25° C.) after 2 hours time. Checking the product under a UV lamp after drying a small sample on a substrate with a heat gun indicated it to be the inactive salt derivative; no blue coloration developed until treated with water followed by UV light.

(2) To 5 mls acetic acid, 0.9 g (0.008 mol, 18 wt %) $CaCl_2$ was dissolved with heating. Simultaneously, 1.7 g 1KPR and 3.4 g 1KE were added while stirring and heating for a $CaCl_2$:1KE mole ratio of 0.41:1. On cooling to 25° C., the product precipitated in the form of a particle-gel-like mass which was filtered and washed with petroleum ether (50°–110° C.) then air dried; color: orange-tan.

Testing and Results for #2

(1) Under a UV lamp, it changed to a pale blue after 15 minutes indicating some uncomplexed material; normal KX32(121) changes to a dark blue in less than 1 minute.
(2) Comparing a sample of the product after activation with water with standard 1KE at 80° C. indicated that the product was slightly slower than the standard 1KE.

Conclusion

The preferred minimum mole ratio between $CaCl_2$ and the monomer (1KPR plus 1KE) appears to be 0.5:1, respectively. In procedure #1, this ratio was used and was completely inactive to UV light; in procedure #2, a 0.41:1 ratio was used and was partially active.

EXAMPLE VI

REACTIVATION OF INACTIVATED COMPOUNDS WITH VARIOUS SOLVENTS

Though the inactive adduct is obtained for the $CaCl_2$ salts of 1KE and co-crystallized 1KPR/1KE which can be regenerated to their active form using water, other solvents such as methanol appear to have the same reactivation effect.

1KE (8 g, 0.032 mol) was dissolved with heating in 10 ml acetic acid/$CaCl_2$ (1.8 g 0.016 mol). The cooled product formed a syrup which particularized after adding methanol (20 ml). After filtering and washing with small quantities of additional methanol, it was checked under a UV lamp. Results: Prior to precipitation with MeOH, a sample of the syrup was set on a substrate and dried with a heat-gun then checked under a UV lamp; it remained inactive. The testing of another sample after preciptation and work-up with MeOH under a UV lamp indicated that it was active by the fact that it changed to blue. Surpisingly, even though the intial media solvent was MeOH, the addition of additional MeOH during the work-up resulted in an active product.

EXAMPLE VII

COMPATABILITY STUDY FOR OBTAINING THE INACTIVE $CaCl_2$ AND LiCl DERIVATIVE OF 1KE IN VARIOUS WATER SOLUBLE BINDERS

Some of the $CaCl_2$ and especially the LiCl derivatives of 1KE and 1KPR/1KE(1:2) are syrups which can possibly be processed immediately into a water soluble binder (a water soluble binder would allow easy activation with a water based activator) without activation occurring; even as powders, a water soluble polymer would be necessary with a non-protic common solvent The following set of experiments investigates their feasiblity.

EXPERIMENT 1

1KE (2 g, 0.008 mol) was added to a hot solution containing 5 ml acetic acid and LiCl (0.7 g, 0.008 mol, 14 wt %). The solution was checked by dabbing a portion on a substrate and drying with a heat gun then setting it under a UV lamp; it was found to be inactive. 4 g poly(ethylene-glycol), PEG, MW, 8K, was added to the hot solution. The viscous solution was rechecked under a UV lamp. Found: it changed to blue slowly.

The LiCl was increased to 1.4 g (28 wt %) while heating. Results: no UV activity was noted after drying.

EXPERIMENT 2

Repeated Experiment 1 by replacing the LiCl with $CaCl_2$; 0.9 g, 0.008 mol) initially and 1.8 g, 0.016 mol) finally. Also, instead of 4 g PEG, 5 g was used. Checking samples of both the initial and final products under a UV lamp indicated activity; both changed to blue.

EXPERIMENT 3

1KE (1 g, 0.004 mol) was added to a hot solution composed of $CaCl_2$ (0.9 g, 0.008 mol) and (10 ml acetic acid followed by 0.5 g poly(acrylic acid) PAA, MW 250K. The PAA dissolved with difficulty due to its low solubility. A dried sample was checked under a UV lamp; it did not change to blue, but instead became yellow, indicating inactivity.

RESULTS

Comparing the LiCl adduct of 1KE with the $CaCl_2$ adduct in PEG binder using acetic acid as solvent resulted in UV activity when the $CaCl_2$ wt % was 14 and 28% and the LiCl wt % was 14%. When the LiCl concentration was 28 wt %, no activity was noted under a UV lamp. The 1KE/$CaCl_2$ derivative became inactive when the PEG binder was replaced with the PAA binder. Here, the wt % of the $CaCl_2$ was 18% but the amount of PAA which could be solubilized was only 10 wt % as compared to the 80 and 100 wt % for Exp. 1 & 2 respectively. The results further indicate that inactivity is possible only when a balance of concentrations and conditions are maintained.

EXAMPLE VIII

PHYSICAL PROPERTIES AND UV ACTIVITY OR INACTIVITY OF 1KPR/1KE(1:2)/$CaCl_2$ COMPLEX IN ACETIC ACID AND MeOH FROM VARYING THE MOLE RATIO BETWEEN $CaCl_2$ TO THE 1KPR/1KE(1:2) MONOMERS AND ALSO THE $CaCl_2$ TO SOLVENT WT %

The wt % of the $CaCl_2$ in MeOH and acetic acid is an important parameter, as to whether the 1KE or cocrystallized 1KPR/1KE will be active or inactive. The preferred wt % of $CaCl_2$ was investigated.

EXPERIMENTAL PROCEDURE (1) For Table Va: The $CaCl_2$ (and LiCl, see Section X) was dissolved in hot acetic acid or MeOH. To the hot solutions, a 1:2 ratio of 1KPR:1KE was added in one-shot with stirring and heated to a boil. After dissolution (or emulsification), it was immediately poured into a 1 oz. jar and tested (see Table) under a UV lamp. Prior to testing the samples were applied to a filter paper substrate and dried with a heat gun.

(2) For Table Vb: Same as for Table Va except that the medias were cooled in a cold water bath to 20° C. to 25° C. and isolated by filtration followed by washing with petroleum ether (50°–110° C.) followed by vacuum drying for 2 hours at 25° C.

(3) For Table Vc: Same as Table Va for samples that could not be isolated and Table Vb for samples that could be isolated.

TABLE Va

| UV ACTIVITY AND PHYSICAL APPEARANCE OF 1KPR/1KE(1:2)/$CaCl_2$ AS A FUNCTION OF A VARIATIONS OF SOLVENT, MONOMER AND SALT CONCENTRATION | | | | | | |
|---|---|---|---|---|---|---|
| Sample # | $CaCl_2$ g/mol/wt % | Solvent/mls | Monomers 1KPR(g)/1KE(g) wt % | UV Active | Physical Appearance (22° C.) | mol ratio $CaCl_2$:MON |
| 1 | 0.9/0.008/9 | MeOH/10 | 0.75/1.5/22.5 | No | solid particles | 1.0 |
| 2 | 1.8/0.016/36 | Acetic Acid/5 | 0.75/1.5/45 | No | slurry | 2.0 |
| 3 | 0.9/0.008/18 | Acetic Acid/5 | 0.75/1.5/45 | No | semi-viscous | 1.0 |
| 4 | 0.45/0.004/9 | Acetic Acid/5 | 0.75/1.5/45 | Yes | wet crystalline solid | 0.5 |
| 5 | 0.45/0.004/9 | Acetic Acid/5 | 1.5/3.0/90 | Yes | insufficient solubility | 0.2 |
| 6 | 0.9/0.008/18 | Acetic Acid/5 | 1.5/3.0/90 | No | wet-crystalline solid | 0.5 |
| 7 | 0.9/0.008/18 | Acetic Acid/5 | 1.5/3.0.90 | No | isolated with P. ether | 0.5 |

Results

Comparing samples #4, 6, and 7 with a mole ratio of 0.5:1 between the $CaCl_2$:monomers, only when the wt % of the $CaCl_2$ to solvent was 18 wt % (samples #6 and #7) rather than 9 wt % (sample #4) was the product inactive to UV light. This should be contrasted with sample #1, where methanol was used instead of acetic acid. 9 wt % value also resulted in an inactive product in this case.

In order to be isolatable, the product must form a wet-crystalline solid such as obtained in sample #6 which was repeated in sample #7 followed by filtration and washing with pet. ether (50°–110° C.).

UV ACTIVITY OR INACTIVITY OF VARIOUS CONCENTRATIONS OF KPR/1KE AND CaCl₂ KEEPING THE MOLE RATIO BETWEEN CaCl₂:(1KPR + 1KE) CONSTANT AT 0.5:1, RESPECTIVELY IN 5 ML ACETIC ACID

| Sample # | 1KPR g(mmol) | 1KE g(mmol) | CaCl₂ g(mmol) | Mol Ratio CaCl₂:MON. | wt % MON. | wt % CaCl₂ | wt % Ratio MON.:CaCl₂ | UV Active |
|---|---|---|---|---|---|---|---|---|
| 8 | 0.75(2.7) | 1.5(6.0) | 0.48(4.3) | 0.5:1 | 45 | 9.6 | 4.7 | Yes |
| 9 | 1.0(3.6) | 2.0(8.0) | 0.64(5.8) | 0.5:1 | 60 | 12.9 | 4.7 | Yes, slight |
| 10 | 0.13(4.0) | 2.25(9.0) | 0.72(6.5) | 0.5:1 | 67.5 | 14.4 | 4.7 | No |
| 14 | 1.5(5.4) | 3.0(12.0) | 0.97(8.7) | 0.5:1 | 90 | 19.4 | 4.7 | No |

MON. is the monomer combination of 1KE and 1KPR.

Results

When the wt % of CaCl₂ in acetic acid (5 ml) was 9.6 and 12.9, UV activity occurred, whereas for the 14.4 and 19.4, it did not. Comparing the 14.4 with the 19.4 CaCl₂ wt %'s, better mixability occurs during complexation of the 14.4 wt % than for the 19.4 wt % material.

TABLE Vc

EFFECTS OF THE MOLE RATIO BETWEEN CaCl₂:MONOMER ON THE PROCESSIBILITY OF THE

COCRYSTALLIZED 1KPR/1KE(1:2)/CaCl₂

| Sample # | 1KPR g(mmol) | 1KE g(mmol) | CaCl₂ g(mmol) | Mol Ratio CaCl₂:MON. |
|---|---|---|---|---|
| 12 | 1.13(4.50) | 2.25(9.00) | 0.72(6.49) | 0.5:1 |
| 13 | 0.84(3.02) | 1.69(6.76) | 0.72(6.49) | 0.75:1 |
| 14 | 0.56(2.01) | 1.13(4.50) | 0.72(6.49) | 1:1 |
| 15 | 0.28(1.00) | 0.56(2.24) | 0.72(6.49) | 2:1 |
| 16 | 1.0(3.60) | 2.0(8.00) | 90.97(8.74) | 0.75:1 |
| 17 | 1.0(3.60) | 2.0(8.00) | 0.77(6.94) | 0.6:1 |

NOTE:
All of the above samples are inactive to UV light after applying a small portion on a substrate followed by drying with a heat gun.

Results

Only when the mole ratio between the CaCl₂:monomer was equal to 0.5:1, respectively was the resultant product processible.

Conclusion

For a preferred inactive product, the mole ratio between the CaCl₂:monomer should be 0.5:1, respectively with a 14.4 wt % CaCl₂ in acetic acid.

EXAMPLE IX

PHYSICAL PROPERTIES AND UV ACTIVITY OR INACTIVITY OF 1KPR/1KE(1:2)/LiCl COMPLEXES IN ACETIC ACID AND MeOH FROM VARYING THE MOLE RATIO BETWEEN THE LiCl TO 1KPR/1KE MONOMERS AND ALSO THE LiCl TO SOLVENT WT %

Experiments were performed employing parameter limitations similar to the above. The following table summarizes the results.

TABLE VI

UV BEHAVIOR AND PHYSICAL APPEARANCE OF 1KPR/1KE(1:2)/LiCl AS A FUNCTION OF VARIATIONS OF SOLVENT, MONOMER QUANTITY, AND LiCl CONCENTRATION

| Sample # | LiCl G/mol/wt % | Solvent/ml | Monomers(MON) 1KPR(g)/1KE wt % | UV Active | mol ratio LiCl:Mon | Physical Appearance (22° C.) |
|---|---|---|---|---|---|---|
| 1 | 0.7/0.017/14 | Acetic Acid/5 | 0.75/1.5/45 | Partial | 2:1 | liquid |
| 2 | 0.7/0.017/14 | MeOH/5 | 0.75/1.5/45 | Yes | 2:1 | solid-particles |
| 3 | 1.4/0.033/14 | IPA/10 | 0.75/1.5/22.5 | Slight | 4:1 | liquid |
| 4 | 1.4/0.033/28 | MeOH/5 | 0.75/1.5/45 | No | 4:1 | liquid |
| 5 | 0.7/0.017/14 | Acetic Acid/5 | 1.5/3.0/90 | Yes | 1:1 | solid-particles |
| 6 | 0.7/0.017/14 | MeOH/5 | 1.5/3.0/90 | Yes | 1:1 | solid-particles |
| 7 | 1.4/0.033/28 | MeOH/5 | 1.5/3.0/90 | Slight | 2:1 | solid-particles |

Results

The only sample which indicated complete inactivity was sample #4. The important parameters, here, appear to be the high ratio between the LiCl:monomer which is 4:1, and the high wt % of the LiCl in the MeOH (28 wt %). Problem: If there is residual LiCl, reactivation is expected in the long term due to the hygroscopicity of LiCl (the inactive form is readily activated with water).

EXAMPLE X

ACTIVITY OF 1KPR/1KE WITH A VARIETY OF SALTS DERIVED FROM GROUP I AND II METALS

Additional salts of groups I and II metals were investigated for the purpose of finding other 1KPR/1KE(1:2) dervvatives which remain inactive after complexing.

The procedure ws the same as described above. All pertinent information is shown in the following table.

TABLE VII

UV BEHAVIOR AND PHYSICAL APPEARANCE OF 1KPR/1KE(1:2) USING A VARIETY OF GROUP I AND Group II METAL SALTS

| Sample # | Salt | g/moles | Solvent/ml | 1KPR/1KE (g) (g) | UV Active | Physical Appearance (22° C.) |
|---|---|---|---|---|---|---|
| 1 | NaOOCCH₃ | 0.95/0.012 | Acetic Acid/10 | 0.75/1.5 | Yes | solid |
| 2 | LiBr | 1.4/0.016 | Acetic Acid/5 | 0.75/1.5 | Yes | liquid |
| 3 | NaI | 1.2/0.008 | Acetic Acid/5 | 0.75/.5 | Yes | liquid |
| 4 | MgCl₂ | 0.7/0.007 | Acetic Acid/5 | 1.3/2.6 | Yes | |
| 5 | SrCl₂ | 1.3/0.008 | MeOH/10 | 0.5/1.0 | Yes | solid |

TABLE VII-continued

UV BEHAVIOR AND PHYSICAL APPEARANCE OF 1KPR/1KE(1:2) USING A VARIETY OF GROUP I AND Group II METAL SALTS

| Sample # | Salt | g/moles | Solvent/ml | 1KPR/1KE (g) (g) | UV Active | Physical Appearance (22° C.) |
|---|---|---|---|---|---|---|
| 6 | MgCl$_2$ | 1.4/0.015 | Acetic Acid/5 | 0.75/1.5 | Partial | liquid |
| 7 | CsCl | 1.3/0.008 | Acetic Acid/5 | 0.75/1.5 | Yes | solid |

Results: The only sample which indicated partial inactivity was sample #4; the others did not.

EXAMPLE XI

COMPARATIVE THERMAL COLOR RESPONSE AFTER SOLVENT ACTIVATION OF THE INACTIVE 1KPR/1KE (1:2)/CaCl$_2$ WITH STANDARD KX32(121)

As shown above, the color response of the CaCl$_2$ derivatives of 1KPR/1KE(1:2) are much less than the standard co-crystallized fast indicator KX32(121). On the assumption that solvation followed by hydration of the CaCl$_2$ is the mode of reactivation and that possibly reactivation with water as previously used lacks the necessary solvating power, additional activating solvent systems were tested. The effects of the different activating solvent media activators on the inactive 1KPR/1KE/(1:2)/CaCl$_2$ indicator were compared thermally with the standard KX32(121). In this respect, a stepwise approach was taken which is shown in the following tables.

EXPERIMENTAL

Procedure: Sample #7 described in Table Va was applied with a spatula to 1×2 cm filter paper strips. They were wetted with the media shown in the following tables and thermally annealed on a Mettler Hot Stage at 80° C. Also shown is the color development comparison with the standard KX32(121) fast indicator.

TABLE VIII

COMPARATIVE COLOR RESPONSE OF KX32(121) WITH 1KPR/1KE/(1:2)/CaCl$_2$ (SAMPLE #7, Table Va) ACTIVATED BY VARIOUS AQUEOUS SALTS (10%) AND ACETIC ACID (50% aq.) AT 80° C.

| Sample # | Activating Solution | Color Response After 15 min. | 45 min. | Activity Rating |
|---|---|---|---|---|
| 1 | LiCl | lt. blue | med. blue | 1 lowest |
| 2 | MgCl$_2$ | med. blue | med. to dark blue | 2.5 |
| 3 | SrCl$_2$ | med. blue | med. to dark blue | 2 |
| 4 | Acetic Acid | med. to dark blue | blue-black | 3.5 highest |
| KX32(121) | Control | blue | med. to dark blue-black | |

Results: 1KPR/1KE/CaCl$_2$ activated with acetic acid (50%) had the highest color response acitvity; it intensified to a blue-black, which appeared to be faster than the standard KX32(121).

Conclusion: The lower color response activity seems to be due to incomplete reactivation which appears to be rectified by the polar activating media composed of acetic acid and water.

TABLE IX

PRELIMINARY TESTING OF VARIOUS POLAR SOLVENT SYSTEMS FOR ACTIVATING 1KPR/1KE/(1:2)/CaCl$_2$ INDICATOR AND COMPARING THEIR EFFECTS WITH STANDARD KX32(121) AT 80° C.

| Sample | Activator | Color Response After 15 min | 30 min. | Rel. Act. to KX32 (121) |
|---|---|---|---|---|
| 1 | Acetic Acid 50% | med. blue | dark blue | same as |
| 2 | Tartaric Acid (5%) | lt. gray blue | med. gray blue | much less than |
| 3 | Citric Acid (5%) | lt. gray blue | med. gray blue | much less than |
| 4 | Lactic Acid (5%) | lt. gray blue | med. gray blue | much less than |
| 5 | MeOH | lt. to med. blue | med. to dark blue | less than |
| 6 | Isopropanol (IPA) | yellow | yellow | no reactivity |
| 7 | H$_2$O (distilled) | lt. gray blue | med. gray blue | less than |
| 32 (121) | Control | med. blue | dark blue | KX32(121) |

Results: The color response of the acetic acid (50% aq.) was the same as the control KX32(121). Next best was sample #5 activated with MeOH. Samples #2, 3, and 4 activated with tartartic, citric, and lactic acid indicated low activity it should be noted that the concentration levels were low and hence this might not represent a fair assessment. The IPA treated sample #6 indicated no activity.

TABLE X

THERMAL COLOR RESPONSE OF 1KPR/1KE/(1:2)/CaCl$_2$ AFTER ACTIVATION WITH VARIOUS ACETIC ACIDS SOLUTIONS AT 80° C.

| % Acetic Acid (Vol./Vol.) | Color Response After 15 min | 30 min | Relative Activity |
|---|---|---|---|
| 5 | lt. to med. blue | med. blue | 1 |
| 10 | lt. to med. blue | med. blue | 1 |
| 50 | med. blue | dark blue | 2, highest |
| 95 | yellow | yellow | 0, none |
| KX32(121) | med. blue | dark blue | 2, highest |

Results: At low concentrations of acetic acid (5 and 10%), low color response was noted; at high concentration (95%), no color response was noted. Only when the acetic acid concentration was 50%, did it compare to the standard KX32(121) control.

TABLE XI

THERMAL COLOR RESPONSE OF 1KPR/1KE(1:2)/CaCl$_2$ AFTER ACTIVATION WITH SOLVENT MIXTURES DERIVED FROM MeOH, ETOH, IPA, ACETIC ACID, AND DISTILLED WATER AT 80° C.

| # | Solvent Mixtures A | B | C | Color Response After 30 min. | Activity Level |
|---|---|---|---|---|---|
| 1 | MeOH (100%) | — | — | med. to dark blue | 3 |
| 2 | MeOH (50%) | H$_2$O (50%) | — | med. blue | 2 |

TABLE XI-continued

THERMAL COLOR RESPONSE OF 1KPR/1KE(1:2)/CaCl$_2$ AFTER ACTIVATION WITH SOLVENT MIXTURES DERIVED FROM MeOH, ETOH, IPA, ACETIC ACID, AND DISTILLED WATER AT 80° C.

| # | Solvent Mixtures A | B | C | Color Response After 30 min. | Activity Level |
|---|---|---|---|---|---|
| 3 | MeOH (50%) | Acetic Acid (50%) | — | yellow | 0 (lowest) |
| 4 | MeOH (25%) | Acetic Acid (25%) | H$_2$O (50%) | dark blue | 4 (highest) |
| 5 | IPA (50%) | Acetic Acid (50%) | — | yellow | 0 |
| 6 | ETOH (100%) | — | — | yellow | 0 |
| 7 | ETOH (50%) | H$_2$O (50%) | — | lt. blue | 1 |
| 8 | ETOH (40%) | Acetic Acid (10%) | H$_2$O (50%) | med. blue | 2 |
| 9 | ETOH (25%) | Acetic Acid (25%) | H$_2$O (50%) | med. to dark blue | 3 |
| 10 | Control | Control | Control | dark blue | 4 |

Results: The table indicates that only mixture #4 containing MeOH (25%), acetic acid (25%), and H$_2$O (50%) resulted in full restoration of activity for the 1KPR/1KE(1:2)/CaCl$_2$ co-crystallized salt which was equal in color response to the standard KX32(121) and is therefore equivalent to the acetic acid (50%, aq.) shown in Table X. The IPA (50%) plus acetic acid (50%) #5 and surprisingly, the ETOH (100%) #6 and also the acetic acid (50%) plus MeOH (50%) #3 were completely ineffective in this particular case. The remaining entries (#'s 1, 2, 7, 8, and 9) gave partial activation which potentially could be used as cativators for a lower activity indicator, thereby extending the color-response over a longer period of time.

EXAMPLE XII

Calcium Salt of the Butyl Urea Derivative 14.4 wt % CaCl$_2$ in acetic acid was prepared and used as a stock solution for the following experiments. The butyl derivative, 1KB, was dissolved in the CaCl$_2$/acetic acid medias to obtain the mole ratios (shown in the following tables) between the CaCl$_2$ and 1KB, respectively. The table also shows the color-response due to thermal and uv light (15 seconds), and also uv followed by moisture.

TABLE XII

EFFECTS OF VARIOUS MOLE RATIOS BETWEEN CaCl$_2$ AND 1KB ON THE RESULTANT UV, THERMAL AND MOISTURE COLOR RESPONSE

| Mole Ratio CaCl$_2$:1KB | Thermal Activity after 4 hrs. @ 80° C. | Color Change due to Moisture after UV Treatment (15 sec.) |
|---|---|---|
| 1:1 | medium blue | blue-purple→lighter blue-purple |
| 1.13:1 | lt. to med. blue | red-purple→orange (spontan.) |
| 1.3:1 | lt. to med. red-purple | red-purple→orange (spontan.) |
| 2:1 | lt. yellow-orange | red-purple→orange (spontan.) |
| 4:1 | lt. yellow | red→orange (spontaneous) |
| 1KB (control) | dk. black-blue | blue→blue |

Results

When the mole ratios were 2:1 and 4:1 between the CaCl$_2$ and 1KB, respectively, the materials changed to a bright red; whereas thermally very little change was noted after 4 hours at 80° C. On the other hand, the control sample which was not treated with CaCl$_2$ became blue under the same conditions. The above red samples spontaneously changed to orange when contacted with H$_2$O after UV treatment (15 seconds); no change was noted for the control sample.

Comparing the 1:1 and 1.13:1 mole ratios between the CaCl$_2$ and 1KB with the control non-CaCl$_2$ treated sample, a decrease in thermal color-response was noted in the order of 1KB (control) >1:1 sample >1.13:1 sample indicating that the CaCl$_2$ adducts can be used to decrease the color-response of the parent 1 KB composition.

EXAMPLE XIII

Calcium Salt of the Hexyl Urea Derivative

Similar to the butyl urea derivatives, a 14.4 wt % CaCl$_2$/acetic acid stock solution was prepared and used to form the CaCl$_2$ adducts of the hexyl derivatives, 1KH, similarly shown on the following table.

TABLE XIII

Effects of Various Mole Ratios Between CaCl$_2$ and 1KH on the Resultant UV, Thermal and Moisture Color Response

| Mole Ratio CaCl$_2$:1KH | Thermal Activity after 1 hrs. @ 80° C. | Color Change Due to Moisture After UV Treatment (10 sec.) |
|---|---|---|
| 0.5:1 | black-blue | black-blue→black-blue |
| 1:1 | med. blue-purple | dark blue→dark blue |
| 2:1 | lt. to med. blue-purple | red-purple→red-orange (spont.) |
| 4:1 | lt. red-purple | red-purple→orange (spont.) then brown |
| 1KH (control) | pale to lt. blue | med. blue→med. blue |

Results

The thermal activity indicates that the hexyl derivative of the CaCl$_2$ hexyl adduct was less effective in reducing the color-response activity than the butyl derivatives (the ethyl and propyl derivatives indicate no activity).

It is particularly noteworthy that the color-response of the 0.5:1 mole ratio sample was much greater than the 1KH control sample; a useful property for increasing the color response.

EXAMPLE XIV

CaCl$_2$ Salts Of The Higher Urea Derivatives

Similar to the butyl and hexyl urea derivatives, a 14.4 wt % CaCl$_2$/acetic acid stock solution was prepared and used to form the CaCl$_2$ products of the octyl, 1KO; dodecyl, 1KDD; octadecyl, 1KOD; butoxycarbonylmethylene, 1KBCMU; and the ethoxycarbonylmethylene, 1KECMU, derivatives. Tables XIV–XVI indicates the pertinent details.

TABLE XIV

EFFECTS OF VARIOUS MOLE RATIOS BETWEEN $CaCl_2$ AND 1KO ON THE RESULTANT UV, THERMAL, AND MOISTURE COLOR RESPONSE

| Mole Ratio $CaCl_2$:1KO | Thermal Activity after 4 hrs. @ 80° C. | Color Change Due to Moisture after UV Treatment (10 sec.) |
|---|---|---|
| 0.5:1 | black-blue | dark blue→dark blue |
| 2:1 | dark blue-purple | med. dark blue→med. dark blue |
| 4:1 | dark blue-purple | red & blue→red changes to orange |
| 1KO (control) | med. blue | med. blue purple→med. blue purple |

RESULTS

The treatment with $CaCl_2$ on the 1KO derivative had very little effect except in enhancing the color response, especially for the 0.5:1 mole ratio, whereby the color response after 4 hours of thermal treatment was much darker and intense as compared to the 1KO control sample. The 4:1 mole ratio sample indicated some moisture effects due to the $CaCl_2$, whereby a portion of the sample changed from red to orange when treated with moisture after 10 seconds of uv treatment.

TABLE XV

EFFECTS OF VARIOUS MOLE RATIOS BETWEEN $CaCl_2$ AND 1KBCMU ON THE RESULTANT UV, THERMAL AND MOISTURE COLOR RESPONSE

| Mole Ratio $CaCl_2$:1KBCMU | Thermal Activity after 4 hrs. @ 80° C. | Color change due to Moisture after UV Treatment (10 sec.) |
|---|---|---|
| 1:1 | med. to dark blue-purple | med. blue-purple→med. blue-pur. |
| 2:1 | dark blue-purple | med. red-purple→med. tan-orange |
| 4:1 | pale to lt. pink | lt. to med. red→orange |
| 1KBCMU (Control) | med. to dark blue-purple | med. blue→med. blue |

RESULTS

The 1:1 mole ratio sample was not sensitive to moisture after uv treatment, whereas the 2:1 and 4:1 were sensitive. The 2:1 mole ratio was the most color responsive; it changed to a dark blue-purple after 4 hours thermal treatment, whereas the control sample changed to a medium to dark blue purple.

TABLE XVI

EFFECTS OF VARIOUS MOLE RATIOS BETWEEN $CaCl_2$ AND 1KDD, 1KOD, AND 1KBCMU ON THE RESULTANT UV, THERMAL, AND MOISTURE COLOR RESPONSE

| Mole[5] Ratio $CaCl_2$: MON. | Monomer (MON) | Thermal Activity @ 80° C. | Color Change Due to Moisture after UV Treatment (10 sec.) |
|---|---|---|---|
| 0.5:1 purple | 1KDD | med. orange brown (2 hr.) | med. red-purple→med. red- |
| " | " | lt.-med. red brown (2 hr.) | lt.-med. blue purple→lt.-med. blue-purple |
| 4:1 | " | lt.-med. red brown (2 hr.) | med. gray purple→med. gray purple |
| 4:1 | 1KOD | med. red purple | dark blue→dark blue |
| 4:1 | 1KBCMU | med. brown (5 hr.) | med. blue→med. blue |
| Control | 1KDD | med. to dark blue (2 hr.) | dark blue→dark blue |
| " | 1KOD | yellow | yellow→yellow |
| " | 1KECMU | | med. blue→med. blue |

RESULTS (1) The uv color response of all $CaCl_2$ samples was different from the thermal color response. None of the $CaCl_2$ thermally treated samples were in the blue family of colors; therefore, no color response enhancement.

(2) None of the $CaCl_2$ samples were effected by moisture.

EXAMPLE XV $CaCl_2$ Of The Isopropyl Urea, 1KIP, Derivative

Similar to the other urea derivatives, the inactive isopropyl urea, 1KIP, derivative was treated with a 14.4 wt % solution of $CaCl_2$/acetic acid, whereby the solubilized $CaCl_2$ to 1KIP monomer ratios were 0.5:1, 1:1, and 2:1, respectively.

RESULTS

The adducts were found to be inactive except when treated with water which resulted in a white to blue-purple color change when treated with uv light. However, no color change was found when the water treated samples were thermally annealed indicating only uv activity.

Best results were obtained for the 1:1 mole ratio followed by the 0.5:1 then 2:1 mole ratio samples.

EXAMPLE XVI

LiCl SALTS OF THE UREA DERIVATIVES

Similar to the $CaCl_2$ derivatives, LiCl was used as a 14 wt % solution in acetic acid to form the following products. Only a 4:1 solution ratio between the LiCl to the urea monomers, respectively, was used. The following table gives the comparative results between the untreated and the lithium chloride treated monomers for their thermal and uv color response.

TABLE XVII

COMPARATIVE THERMAL COLOR RESPONSE OF THE UNTREATED AND LiCl TREATED UREA DERIVATIVES WHERE THE MOLE RATIO USED WAS 4:1 BETWEEN THE LiCl TO UREA MONOMER, RESPECTIVELY.

| Monomer 4:1 Treated | Color Response at 80° C. | | UV Color Response (10 sec.) |
|---|---|---|---|
| | 0 hr | 1 hr | |
| 1KE (fast)[a] | white | dark blue | — |
| 1KE (slow)[b] | pinkish | medium blue | — |
| 1KE (4:1) | white | black blue | dark blue |
| 1KIP | white | white | — |
| 1KIP (4:1) | white | white | white |
| 1KPR | pinkish | pale blue | — |
| 1KPR (4:1) | white | white | medium yellow |
| 1KB | pale blue | light to med. blue | — |
| 1KB (4:1) | white | light to med. blue | medium blue |
| 1KH | white | pale to light blue | — |
| 1KH (4:1) | lt. blue | dark blue | dark blue-purple |

TABLE XVII-continued
COMPARATIVE THERMAL COLOR RESPONSE OF THE UNTREATED AND LiCl TREATED UREA DERIVATIVES WHERE THE MOLE RATIO USED WAS 4:1 BETWEEN THE LiCl TO UREA MONOMER, RESPECTIVELY.

| Monomer 4:1 Treated | Color Response at 80° C. After 0 hr | 1 hr | UV Color Response (10 sec.) |
|---|---|---|---|
| 1KO | white | pale to light blue | — |
| 1KO (4:1) | lt. blue | med. red-purple | dark blue |
| 1KDD | pale blue | med. red-purple* | — |
| 1KDD (4:1) | white | light red-purple | med. to dark gray blue |
| 1KOD | yellow | yellow | — |
| 1KOD (4:1) | reddish | medium red-maroon | dark blue-purple |
| 1KECMU | pinkish | pale to light blue | — |
| 1KECMU (4:1) | pinkish | pale to light blue | medium to dark blue |
| 1KBCMU | white | light blue-purple | — |
| 1KBCMU (4:1) | lt. blue | dark blue-purple | dark blue-purple |

*changes to blue-purple on cooling to room temperature ambient.
<sup>a</sup>Highly colored responsive phase obtained by recrystallization from acetic acid using a 15 minute reflex cycle before cooling; higher reflex time, e.g., 30 minutes reduce color-responsiveness.
<sup>b</sup>Slower color responsiveness phase obtained by recrystallization from an acetic acid (90%)/H$_2$O (10%) Co-solvent system.

RESULTS

None of the lithium chloride treated samples were moisture sensitive.

Thermally, there was a dramatic increase in color response for the 1KH, 1KO, and IKBCMU.

The 1KPR became inactive; it changed to yellow rather than blue both thermally and under uv.

EXAMPLE XVII

MgCl$_2$ SALTS OF THE UREA DERIVATIVES

Similar to the LiCl treated urea derivatives, the MgCl$_2$ derivatives were prepared using a 4:1 ratio between the MgCl$_2$ to monomer, respectively, employing a 12.2 wt % solution of MgCl$_2$ in acetic acid. The following table indicates the effect of the uv and thermal treatments.

TABLE XVII
COMPARATIVE THERMAL COLOR RESPONSE BETWEEN MgCl$_2$ TREATED UREAS WITH NON-TREATED UREAS AT 80° C. PLUS THE UV COLOR RESPONSE FOR THE MgCl$_2$ TREATED SAMPLES

| Monomer | Thermal Color Response at 80° C. After 1 hour Non-Treated | Treated | UV Color Response of Treated Monomers after 10 seconds |
|---|---|---|---|
| 1KE | med. to dark blue | black-blue | dark blue |
| 1KB | medium blue | medium blue | dark blue |
| 1KPR | light blue | pale blue | dark blue |
| 1KIP | white | white | white |
| 1KH | light blue | dark blue | dark blue |
| 1KO | pale to lt. blue-purple | dark blue | dark blue |
| 1KDD | medium red-purple | yellow | yellow |
| 1KOD | yellow | med. red-purple | dark blue |
| 1KOD | lt. to med. red-purple | light to med. orange-tan | dark blue |
| 1KBCMU | light blue | black-blue | black-blue |
| 1KECMU | lt. to med. red-purple | lt. to med. red-purple | dark blue |

RESULTS (1) Dramatic increase in color response 1KE, 1KH, 1KO, and 1KBCMU.

(2) Decrease in color response 1KPR.

(3) Deactivation: 1KDD, changes to yellow with uv and thermal; 1KECMU has low-thermal activity; thermally it changes to tan whereas under uv it changes to a dark blue.

(4) No effects: 1KB treated and untreated has some color response; 1KIP remained inactive before and after treatment.

(5) Activation: 1KOD was transferred from an inactive yellow phase to an active red-purple phase.

EXAMPLE XVIII

IV. EFFECTS ON THE ROOM TEMPERATURE AMBIENT COLOR RESPONSE FOR SOME UREA DERIVATIVES DUE TO THE PRESENCE OF CERTAIN SALTS.

A. The butyl urea CaCl$_2$ derivatives were left closed vials at room temperature in the dark. The following tables indicate their resulting color response.

TABLE XIX
AMBIENT ROOM TEMPERATURE COLOR RESPONSE FOR THE CaCl$_2$ SALT OF THE BUTYL UREA DERIVATIVES, 1KB, FOR VARIOUS MOLE RATIOS BETWEEN THE CaCl$_2$ TO BUTYL UREA MONOMER AFTER 30 DAYS.

| Mole ratio CaCl$_2$:1KB | Ambient Room Temperature Color Response after 30 days |
|---|---|
| 1.1:1 | light to medium blue |
| 1.3:1 | off-white (same as initial color) |
| 2:1 | pale pink (same as initial color) |
| 4:1 | white (same as initial color) |
| 1KB (control) | light to medium blue |

RESULTS (1) The 1.1:1 mole ratio sample and the control sample both became a light to medium blue after 30 days, indicating a similar color response (2) The 1.3:1, 2:1, and 4:1 mole ratio samples had no room temperature ambient color response after 30 days, indicating stability of the non UV irradiated samples for this period of time.

B. An ambient room temperature color response comparison for the MgCl$_2$ or LiCl treated urea derivatives was conducted and compared with a fast KX32(121) co-crystallized incicator. The derivatives were prepared using a 4:1 mole ratio between the MgCl$_2$ or LiCl to monomer, respectively, and sealed in glass vials. Results indicated an enhancement of color response after the MgCl$_2$ or LiCl treatment after 9 days.

TABLE XX

| Monomer | Color Response After 9 Days at Room Temp. |
|---|---|
| KX32(121), standard | black-blue |
| 1KE/MgCl$_2$ | blue-black |
| 1KH/MgCl$_2$ | medium blue |
| 1KH/LiCl | medium blue |
| 1KO/MgCl$_2$ | medium blue |
| 1KO/LiCl | medium blue |
| 1KBCMU/MgCl$_2$ | dark-blue |
| 1KBCMU/LiCl | medium to dark blue |

RESULTS (1) The 1KE/MgCl (blue-black) exceeded the color response of the standard KX32(121) (black-blue).

(2) The MgCl$_2$ and LiCl treated samples of 1KH and 1KO were similar in color-response; all were a medium blue.

(3) The 1KBCMU/MgCl$_2$ and 1KBCMU/LiCl were a dark blue and medium to dark blue, respectively, and intermediate in color response

ELEMENTAL AND X-RAY ANALYSIS

Elemental analysis indicated that only small amounts of Mg and Li were incorporated in the diureas, as opposed to large amounts of Ca. The Mg ranged from as low as 0.11 to 1.24%. The Li ranged from as low as 0.11 to 0.7%. The Ca ranged from 3.8 to 17.7% (generally increasing the amount of CaCl to monomer in the complexing solution from 0.5:1 to 4:1 moles respectively increased the amounts incorporated CaCl$_2$).

Though only small amounts of the LiCl and MgCl$_2$ were incorporated in the diureas, significant differences were observed in the X-ray patterns of the LiCl and MgCl$_2$ treated samples as compared to the respective non-treated samples.

EXAMPLE XIX

PREPARATION OF THE CALCIUM SALT OF THE ETHYL DERIVATIVE, 1KE 27.8 g (0.25 mol, 14.4 wt %) CaCl$_2$ was dissolved in 193 ml hot acetic acid. The temperature was adjusted to 100° C. then 125 g (0.5 mol) 2,4-hexadiyn-1,6-bis(ethylurea), 1KE, was added slowly with stirring (1:2 mole ratio between the CaCl$_2$ and 1KE, respectively) resulting in immediate dissolution. The solution was raised to the boiling point between 115°-120° C. then removed from the heat source. It was further stirred for an additional 5 minutes then cooled in a cold water bath to 20° C., whereby the product precipitated as a semi-viscous particulate mass.

Work-Up: It was filtered, washed several times with n-hexane. due to agglomeration, it was difficult to remove the solvent. It was then vacuum dried at room temperature for 4 days. YIELD: 152 g (virtually 100%) of light tan product which was insensitive to UV irradiation. Contacting a fresh sample with methanol results in a rapid color change to blue under a UV source and a slow to moderate color change to blue at room temperature ambient.

ELEMENTAL (BASED ON THE PROPORTION USED)

For $C_{12}H_{18}N_4O_2$ (CaCl$_2$)$_{0.50}$(305.795):

Calc: C, 47.13; H, 5.93; N, 18.32; O, 10.46; Ca, 6.55; Cl, 11.59%

Found: C, 47.03; H, 6.30; N, 16.61; O, 14.97; Ca, 5.63; Cl, 9.46%

EXAMPLE XX

PREPARATION OF THE CALCIUM SALT OF THE PROPYL DERIVATIVE, 1KPR 20.8 g (0.187 mol, 8 wt %) CaCl was dissolved in 260 ml hot ascetic acid. 139 g (0.5 mol) 2,4-hexadiyn-1,6-bis(propylurea), 1KPR, was added continuously at 105° to 110° C. with stirring (0.75:2.0 mole ratio between the CaCl$_2$:1KPR). The monomer dissolved readily until about the remaining 20% whereby thickening and a large amount of precipitation of the calcium derivative occurred. The temperature was kept at 110° to 115° C. for an additional 5 minutes then removed from the heat source. At about 100° C., it was set in a cold water bath and cooled with further stirring to 25° C. Work-Up: tne product was filtered, washed with copious amounts of n-hexane, air dried for about 1 hour then vacuum at room temperature for an additional 20 hours. YIELD: 159 g (virtually 100%) pale tan product which changed to yellow under a UV source after 5 minutes indicative of the inactive form. At room temperature ambient, it remains a tan color indefinitely. Adding a few drops of acetic acid (50%, ag) to a small sample followed by UV irradiation results in a blue product in less than 1 minutes time indicating reactiveateability. At room temperature ambient, the reactiveated product changes to blue very slowly, which is characteristic for this derivative.

NOTE: When the mole ratio between the CaCl$_2$ and 1KPR were at 1:2, respectively and the wt % of the CaCl$_2$ in acetic acid was 11 wt %, the product changed to a dark red after 1 to 2 minutes under a UV source; at room temperature ambient it changed slowly to red. However, when the product was activated with the acetic acid solution, it changed to its normal blue color.

ELEMENTAL (BASED ON PROPORTIONS USED)

FOR $C_{14}H_{22}N_4O_2$ (CaCl$_2$)$_{0.375}$(319.976): CaCl: C, 52.55; H, 6.93; N, 17.51; O, 10.00; Ca, 4.70; Cl, 8.31%;

FOUND: C, 52.49; H, 7.36; N, 16.85; O, 12.04; Ca, 4.10; Cl, 7.16%.

Note: Analysis of the reagent grade CaCl$_2$ indicated 33.6% Ca and 61.8% Cl indicating 5.4% OH present accounting for the higher O and lower Cl values obtained.

ANALYSIS OF THE ETHYL AND PROPYL DERIVATIVES

I. The IR indicated sizeable differences between the precursor ureas and their salt derivatives. The comparative results are in the following table.

TABLE I

IR ANALYSIS FOR THE PRECURSOR AND CALCIUM SALTS OF THE ETHYL (1KE) AND PROPYL (1KPR) DERIVATIVES

| Derivative | NH | Shift | CNH | Shift | Carbonyl | Shift |
|---|---|---|---|---|---|---|
| 1KE | 3335 | — | 1587 | — | 1625 | — |
| 1KE/CaCl$_2$ | 3306 3360 | −29 | 1576 | −11 | 1649 | +24 |
| 1KPR | 3317 | — | 1589 | — | 1629 | — |
| 1KPR/CaCl$_2$ | 3206 | −154 −111 | 1576 | −13 | 1647 | +18 |

II. X-ray diffraction patterns (XRD) were taken on a Phillips Automated Diffractometer in the parafocus mode with CuK [alpha] radiation from 1.5° to 50° 2 $\theta$. The scans of the calcium derivatives were found to be different than the precursors indicating that they are structurally different.

EXAMPLE XXI

PREPARATION OF THE CALCIUM SALT OF THE COCRYSTALLIZED ETHYL (1KE) AND PROPYL (1KPR) DERIVATIVES 21.6 g (0.195 mol, 14.4 wt %) CaCl was dissolved in 150 ml hot acetic acid. 67.5 g (0.27 mol) 1KE and 33.75 g (0.12 mol) 1KPR were premixed and added gradually at 100° C. (1:2 weight ratio between the 1KPR and 1KE, respectively). The temperature was raised to the boiling point (115° to 120° C.) then maintained at 115° C. with stirring for an additional 5 minutes resulting in some precipitation to occur in the orangy colored medium. It was then set in a cold water bath and cooled to 20°-25° C. Work-Up: The product was filtered, washed several times with n-hexane After air-drying for 1 hour, it was set in a vacuum oven at room temperature for 5 hours YIELD: 125 g (Virtually 100%) light tan product which was unaffected by UV light until activated by contact with methanol whereby it changed to blue immediately under a UV source.

ELEMENTAL ANALYSIS

Found: C, 46.91; H, 5.81; N, 17.01; Cl, 8.65: Ca, 5.51; O, 16.11%.

X-ray and IR analysis confirmed the procuct.

EXAMPLE XXII

COCRYASTALLIZATION OF THE ETHYL DERIVATIVE (1KE) WITH THE OCTYL DERIVATIVE (1KO) USING COMPLEXATION AND DECOMPLEXATION TECHNIQUES

As the side chain of the monomers increase, increasingly amounts of solvents are required for recrystallizations. For example, the 1KO derivative requires 15-20 ml acetic acid per gram, whereas the propyl derivative, 1KPR requires 5 ml/gm. The use of Group I and Group II salts increases the solubilization properties of the solutions, thereby reducing the amounts of solvent required. Complexation which occurs during the recrystallization can be easily reversed by the addition of decomplexing solvents such as methanol, water, and acetic acid after precipitation occurs.

The technique was applied to the cocrystallization of a layer side chained octyl derivative 1KO with a smaller side chained ethyl derivative 1KE. Here, the cocrystallized product was obtained by dissolving 1:1, 2:1, 1:2, and 1:4 mole ratios between the 1KO and 1KE, respectively in acetic acid solutions composed of 5% $CaCl_2$ whereby the combined monomer content was 10 wt %. After recrystallization, all that was required was several MeOH washings to assure that the active form was present.

Results indicated that the color response of the 1:1 and the 2:1 ratios exceeded that of the 1KO and the 1KE alme, whereas the 1:2 and the 1:4 were less color responsive.

X-ray analysis confirmed that the product were actually cocrystallized as opposed to being a mixture.

We claim:

1. An acetylenic complex comprising at least one effective complexing metal ion and at least one acetytenic compound of the general formula

Wherein:
a is 1 or 2, b is a whole number from 0 to 5, c is 0 or 1; with the proviso that when a is 1, b and c are 0; and R is $—(CH_2)_n—NHC(O)NHR'$ Wherein
(1) n is an integer of about 1 to 10; and
(2) R' is selected from the group consisting of:
(a) hydrogen;
(b) cycloalkyl;
(c) alkenyl;
(d) cycloalkenyl;
(e) alkyl;
(f) phenyl;
(g) alkoxy;
(h) alkoxyalkyl; and
(i) alkoxy carbonylalkyl.

2. A complex in accordance with claim 1 wherein said acetylenic compound is of the structure:

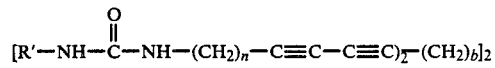

wherein R' is an organic moiety selected from the group consisting of a cycloalkyl moiety of about 3–7 carbon atoms, an alkenyl moiety of about 3–18 carbon atoms, a cycloalkenyl moiety of about 3–7 carbon atoms, an alkoxy moiety of about 2–18 carbon atoms, a linear or branched alkyl moiety of about 1 to 18 carbon atoms, and an alkoxycarbonylmethylene moiety of about 3–14 carbon atoms; n is an integer of about 1 to 5; and 6 is an integer of about 1 to 6.

3. A complex in accordance with claim 1 wherein said acetylenic compound is of the structure:

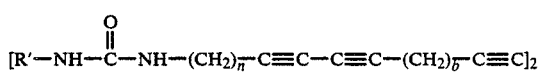

wherein R' is an organic moiety selected from the group consisting of a cycloalkyl moiety of about 3–7 carbon atoms, an alkenyl moiety of about 3–18 carbon atoms, a cycloalkenyl moiety of about 3–7 carbon atoms, an alkoxy moiety of about 2–18 carbon atoms, a linear or branched alkyl moiety of about 1 to 18 carbon atoms, and an alkoxycarbonylmethylene moiety of about 3–14 carbon atoms; n is an integer of about 1 to 4 and 6 is an integer of about 1 to 6.

4. A complex in accordance with claim 1 wherein R' is a linear alkyl moiety of about 4 to 18 carbon atoms and the effective complexing metal ion is derived from $CaCl_2$.

5. A complex in accordance with claim 4 wherein R' is a linear alkyl moiety of about 4–8 carbon atoms.

6. A complex in accordance with claim 5 wherein R' is a linear or branched alkyl moiety of about 1–18 carbon atoms, or an alkoxycarbonylmethylene moiety of about 3–14 carbon atoms.

7. A complex in accordance with claim 1 wherein R' is a linear alkyl moiety of about 1–4 carbon atoms and the effective complexing metal ion is derived from $CaCl_2$.

8. A complex in accordance with claim 7 wherein R' is an ethyl moiety.

9. A complex in accordance with claim 7 wherein R' is selected from the group consisting of ethyl and propyl moieties.

10. A complex in accordance with claim 9 wherein R' contains at least one ethyl moiety and at least one propyl moiety.

11. A complex in accordance with claim 10 wherein the mole ratio of the ethyl moiety to the propyl moiety is about 2:1.

12. A complex in accordance with claim 1 wherein said acetylenic compound is of the structure:

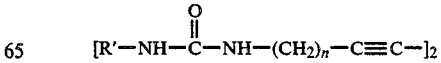

wherein R' is an organic moiety selected from the group consisting of a cycloalkyl moiety of 3–7 carbon atoms, an alkoxy moiety of about 3-7 carbon atoms, an alkenyl moiety of 3-18 carbon atoms, a cycloalkenyl moiety of about 3-7 carbon atoms, an alkoxy moiety of about 2-18 carbon atoms, a linear or branched alkyl of about 2-18 carbon atoms, a linear or branched alkyl moiety of about 1 to 18 carbon atoms, and an alkoxycarbonylmethylene moiety of about 3-14 carbon atoms; and n is an integer of about 1 to 5.

13. A complex in accordance with claim 12 wherein R' is a linear alkyl moiety of about 1-18 carbon atoms.

14. A complex in accordance with claim 12 wherein R' is a linear or branched alkyl moiety of about 1-18 carbon atoms, or an alkoxycarbonylmethylene moiety of about 3-14 carbon atoms.

15. A complex in accordance with claim 14 wherein said complexing metal ion is an ion selected from the group consisting of metals from Group IA, Group IIA, and the transition metals.

16. A complex in accordance with claim 15 wherein said complexing metal ion is derived from the group consisting of Group IA metals.

17. A complex in accordance with claim 15 wherein said complexing metal ion is derived from the group consisting of Group IIA metals.

18. A complex in accordance with claim 15 wherein said complexing metal ion is derived from the group consisting essentially of iron, cobalt, nickel, copper, zinc, cadmium, and tin.

19. A complex in accordance with claim 15 comprising at least two acetylenic compounds.

20. A complex in accordance with claim 19 wherein in a first of said at least two acetylenic compounds, R' is ethyl and in a second of said at least two acetylenic compounds, R' is propyl.

21. An environmental exposure indicating device comprising a substrate having deposited thereon a complex in accordance with claim 1; said complex on said substrate capable of undergoing one or more color changes upon exposure to environmental stimuli to indicate changes in environmental conditions.

22. An environmental exposure indicating device in accordance with claim 21 capable of undergoing one or more color changes upon exposure to moisture.

23. A method of controlling the reactivity of acetylenic compounds of the general formula:

$$[R-(C\equiv C)_a-(CH_2)_b-(C\equiv C)_c]_2$$

Wherein:
 a is 1 or 2, b is a whole number from 0 to 5, c is 0 or 1; with the proviso that when a is 1, b and c are 0; and R is:

$-(CH_2)_n-NHC(O)NHR'$

Wherein:
(1) n is an integer of about 1 to 10; and
(2) R' is selected from the group consisting of:
  (a) hydrogen;
  (b) cycloalkyl;
  (c) alkenyl;
  (d) cycloalkenyl;
  (e) alkyl;
  (f) phenyl;
  (g) alkoxy;
  (h) alkoxyalkyl; and
  (i) alkoxycarbonylalkyl;

said method comprising the step of contacting the compound with an effective complexing metal for a time sufficient to produce an acetylenic complex having a reactivity to environmental stimuli which differs from the reactivity of said acetylenic compound to said stimuli.

24. A method in accordance with claim 23 wherein the complexing metal is selected from the group consisting of metals from Group IA, Group IIA and the transition metals in the Periodic Table.

25. A method in accordance with claim 24 wherein the reactivity of said acetylenic complex to environmental stimuli is greater than that demonstrated by the actylenic compound in the absence of complexation.

* * * * *